(12) United States Patent
Murase et al.

(10) Patent No.: US 8,927,517 B2
(45) Date of Patent: *Jan. 6, 2015

(54) FACTORS CONTROLLING SKIN AND HAIR COLOR

(71) Applicant: Kao Corporation, Tokyo (JP)

(72) Inventors: Daiki Murase, Mason, OH (US); Akira Hachiya, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,374

(22) Filed: Apr. 8, 2013

(65) Prior Publication Data

US 2013/0324587 A1    Dec. 5, 2013

Related U.S. Application Data

(60) Provisional application No. 61/639,489, filed on Apr. 27, 2012.

(51) Int. Cl.
*A61K 48/00*     (2006.01)
*C12Q 1/68*      (2006.01)
*G01N 33/68*     (2006.01)
*G01N 33/50*     (2006.01)

(52) U.S. Cl.
CPC ............ *G01N 33/68* (2013.01); *G01N 33/5044* (2013.01)
USPC ....................................... 514/44 R; 435/6.13

(58) Field of Classification Search
None
See application file for complete search history.

(56) References Cited

U.S. PATENT DOCUMENTS

2006/0116505 A1*  6/2006  Inui et al. ................... 530/350
2013/0243713 A1   9/2013  Murase et al.

FOREIGN PATENT DOCUMENTS

WO    WO 2012/060323 A1    5/2012

OTHER PUBLICATIONS van den Boorn et al, Skin-Depigmenting Agent Monobenzone Induces Potent T-Cell Autoimmunity toward Pigmented Cells by Tyrosinase Haptenation and Melanosome Autophagy, published online Feb. 17, 2011, Journal of Investigative Dermatology, 131: 1240-1251.*
"Whitening strategy. External preparation for whitening," in Advanced Cosmetic Dermatology, IV. Clinical pharmacology of skin whitening agent ("Bihaku senryaku, IV. Bihakuzaino yakuri to rinsho"), Y. Miyachi et al., eds., Nakodo Co., Ltd, Japan, pp. 99-101 (2006).
Thong, Hy et al., "The patterns of melanosome distribution in keratinocytes of human skin as one determining factor of skin colour," Br J Dermatol 149(3): 498-505, (Sep. 2003), Blackwell Scientific Publications, Oxford, England.
Lin, CB et al., "LIGR, a protease-activated receptor-2-derived peptide, enhances skin pigmentation without inducing inflammatory processes," Pigment Cell Melanoma Res 21(2): 172-183, (Apr. 2008), Blackwell Munksgaard, Oxford, England.
Babiarz-Magee, L et al., "The expression and activation of protease-activated receptor-2 correlate with skin color," Pigment Cell Res 17(3): 241-251 (Jun. 2004), Munksgaard International Publishers, Copenhagen, Denmark.
Seiberg, M et al., Inhibition of melanosome transfer results in skin lightening. J Invest Dermatol 115(2): 162-167, (Aug. 2000), Williams and Wilkins, Baltimore, MD.
Seiberg, M et al., "The protease-activated receptor 2 regulates pigmentation via keratinocyte-melanocyte interactions," Exp Cell Res 254(1): 25-32, (Jan. 2000), Academic Press, New York, NY.
Seiberg, M, "Keratinocyte-melanocyte interactions during melanosome transfer," Pigment Cell Res 14(4): 236-242, (Aug. 2001), Blackwell Munksgaard, Oxford, England.
Paine, C et al., "An alternative approach to depigmentation by soybean extracts via inhibition of the PAR-2 pathway," J Invest Dermatol 116(4): 587-595, (Apr. 2001), Williams & Wilkins, Baltimore, MD.
Byers, HR et al., "Role of cytoplasmic dynein in perinuclear aggregation of phagocytosed melanosomes and supranuclear melanin cap formation in human keratinocytes," J Invest Dermatol 121(4): 813-820, (Oct. 2003), Williams & Wilkins, Baltimore, MD.
Byers, HR et al., "Requirement of dynactin p150$^{Glued}$ subunit for the functional integrity of the keratinocyte microparasol," J Invest Dermatol 127(7): 1736-1744, (Jul. 2007), Nature Publishing Group, New York, NY.
Singh, SK et al., "Melanin transfer in human skin cells is mediated by filopodia—a model for homotypic and heterotypic lysosome-related organelle transfer," FASEB J 24: 3756-3769, (Oct. 2010), Federation of American Societies for Experimental Biology, Bethesda, MD.
Ebanks, JP et al., "Epidermal keratinocytes from light vs. dark skin exhibit differential degradation of melanosomes," J Invest Dermatol 131(6): 1226-1233, (Jun. 2011), Nature Publishing Group, New York, NY.
Levine B et al., "Autophagy in the pathogenesis of disease," Cell 132(1): 27-42, (Jan. 2008), Cell Press, Cambridge, MA.
Mizushima, N et al., "Autophagy fights disease through cellular self-digestion," Nature 451(7182): 1069-1075, (Feb. 2008), Nature Publishing Group, New York, NY.
Rubinsztein, DC, "The roles of intracellular protein-degradation pathways in neurodegeneration" Nature 443(7113): 7080-786, (Oct. 2006), Nature Publishing Group, New York, NY.
Mizushima, N et al., "Methods in mammalian autophagy research," Cell 140(3): 313-326, (Feb. 2010), Cell Press, Cambridge, MA.
Mizushima, N et al., "How to interpret LC3 immunoblotting," Autophagy 3(6): 542-545, (Nov. 2007), Landes Bioscience, Georgetown, TX.

(Continued)

*Primary Examiner* — Tracy Vivlemore
*Assistant Examiner* — Kate Poliakova
(74) *Attorney, Agent, or Firm* — Sterne, Kessler, Goldstein & Fox P.L.L.C.

(57)    ABSTRACT

Use of autophagic activity in regulation of the amount of melanin in a keratinocyte, the control of skin or hair color, or selection of an agent for regulating the amount of melanin in a keratinocyte or an agent for controlling skin or hair color.

10 Claims, 11 Drawing Sheets

(56) References Cited

OTHER PUBLICATIONS

Kirkin, V et al., "A role for NBR1 in autophagosomal degradation of ubiquitinated substrates," Mol Cell 33(4): 505-516, (Feb. 2009), Cell Press, Cambridge, MA.
International Search Report (ISR) for PCT/JP2013/062439; I.A. fd: Apr. 26, 2013, mailed Aug. 2013 from the Japanese Patent Office, Tokyo, Japan.
Sceti K.K., "Detoxification of cells by the automatic fuzzy," ("Seti Kabushiki Kaisha, Auto Fuzzy ni yoru Saibo no detox 'CELLDETOX'"), Fragrance J, 2010, vol. 38, No. 8, pp. 121-122, Fureguransujanaru Co., Inc., Japan.
Schiaffino, MV, "Signaling pathways in melanosome biogenesis and pathology," Int J Biochem Cell Biol, Jul. 2010; 42(7): 1094-1104, Elsevier, Amsterdam, Netherlands.
Matsunaga, K et al., "Evolution and relationship to diseases of autophagic driving/regulation machinery," (Shikkan hi Taiko suru Auto Fuzzy Auto Fuzzy no Kudo Seigyo Kiko no Shinka to Shikkan tono Kakawari), Experimental Medicine, 2009, vol. 27, No. 18, pp. 2930-2936, Yodosha Company Limited, Tokyo, Japan.
Itakura, E. et al., ""Physiological role and regulation of mammalian autophagy," (Shikkan ni Taiko suru Auto Fuzzy Honyurui Auto Fuzzy no Seigyo to Seiri Kino"), Experimental Medicine, 2009, vol. 27, No. 18, pp. 2937-2942, Yodosha Company Limited, Tokyo, Japan.
Bryant, DM et al., "A molecular network for de novo generation of the apical surface and lumen," Nat Cell Biol 12(11): 1035-1045, (Nov. 2010), Macmillan Magazines Ltd., London, England.
Gebhardt, C et al., "c-Fos-dependent induction of the small ras-related GTPase Rab11a in skin carcinogenesis," Am J Pathol 167(1): 243-253 (Jul. 2005), American Assn. of Pathologists, Philadelphia, PA.
Ishida-Yamamoto, A et al., "Rab11 is associated with epidermal lamellar granules," J Invest Dermatol 127(9): 2166-2170 (Sep. 2007), Nature Publishing Group, New York.
Komatsu, M et al., "Impairment of starvation-induced and constitutive autophagy in $Atg7$-deficient mice," J. Cell Biol. 169: 425-434 (May 2005), Rockefeller University Press, New York.
Matsunaga, K et al., "Two Beclin 1-binding proteins, Atg14L and Rubicon, reciprocally regulate autophagy at different stages," Nat Cell Biol; 11(4): 385-396, (Apr. 2009), Macmillan Magazines Ltd., London, England.
Progida, C et al., "Rab7b controls trafficking from endosomes to the TGN," J Cell Sci 123: 1480-1491, (May 2010), Company of Biologists, Cambridge, England.
Raymond, A-A et al., "Lamellar Bodies of Human Epidermis: Proteomics Characterization by High Throughput Mass Spectrometry and Possible Involvement of CLIP-170 in their Trafficking/Secretion," Mol. Cell. Proteomics 7: 2151-2175 (Nov. 2008), American Society for Biochemistry and Molecular Biology, Bethesda, MD.
Vaughan, KT et al., "Colocalization of cytoplasmic dynein with dynactin and CLIP-170 at microtubule distal ends," J. Cell Sci 112: 1437-1447 (May 1999), Company of Biologists, Cambridge, England.
Wang, Y et al., "Lysosome-associated small Rab GTPase Rab7b negatively regulates TLR4 signaling in macrophages by promoting lysosomal degradation of TLR4," Blood 110: 962-971 (Aug. 2007), Am. Soc. Hematology, Washington, DC.
Yang, M et al., "Rab7b, a novel lysosome-associated small GTPase, is involved in monocytic differentiation of human acute promyelocytic leukemia cells," Biochem Biophys Res Commun 318(3): 792-799 (Jun. 2004), Academic Press, San Diego, CA.
Yao, M et al, "Late Endosome/Lysosome-Localized Rab7b Suppresses TLR9-Initiated Proinflammatory Cytokine and Type I IFN Production in Macrophages," J Immunol 183: 1751-1758, (Aug. 2009), American Association of Immunologists, Baltimore, MD.
International Search Report (ISR) for PCT/JP2011/075064; I.A. fd: Oct. 31, 2011, mailed Jan. 31, 2012 from the Japanese Patent Office, Tokyo, Japan.
International Preliminary Report on Patentability (IPRP), Chapter I of the Patent Cooperation Treaty, including the Written Opinion for PCT/JP2011/075064; I.A. fd: Oct. 31, 2012, issued May 13, 2013, from the International Bureau of WIPO, Geneva, Switzerland.
Zhuang, Shuzhen et al., "Study on the IZP3 mRNA expression after siRNA interference," Chinese Agricultural Science Bulletin 23(6):23-27 (Jun. 30, 2007), Zhongguo nong xue hui, Beijing, China.
Jiang, Jian et al., "Inhibitory effect of interfering RNA targeting HIF-1 α and VEGF on retinal neovascularization in the mouse," Chin. J. Opthalmol. 44(10):921-928 (Oct. 31, 2008), Chinese Medical Association, Beijing, China.
Ou, Shu-An et al., "Inhibitory effect of Slug gene silencing with siRNA on pancreatic cancer," World Chinese Journal of Digestology, Issue 17, pp. 1713-1719 (Jun. 18, 2009), WJC Press, Beijing, China.
Ho, H. et al., "WIPI1 Coordinates Melanogenic Gene Transcription and Melanosome Formation via TORC1 Inhibition," J. Biol. Chem., Apr. 2011; 286: 12509-12523, Am. Soc. for Biochem. and Molec. Biol., Rockville, MD.
Extended European Search report for EP Appl. No. 11837973.4, including the supplementary European search report and the European search opinion, dated Apr. 4, 2014, European Patent Office, Munich, Germany.
Lacour, JP, "Culturing Human Melanocytes," Pathol Biol (Paris), Feb. 1992; 40(2): 114-120, Elsevier, Paris, France.
Duval, C et al., "Keratinocytes control the pheo/eumelanin ratio in cultured normal human melanocytes," Pigment Cell Res, Dec. 2002; 15(6): 440-446, Munksgaard International Publishers, Copenhagen, Denmark.
Ganesan, AK et al., "Genome-wide siRNA-based functional genomics of pigmentation identifies novel genes and pathways that impact melanogenesis in human cells," PLoS Genet, Dec. 2008; 4(12): e1000298, 12 pages, www.plosgenetics.org, Public Library of Science, San Francisco, CA.
Baxter, LL et al., "Networks and pathways in pigmentation, health, and disease," Wiley Interdiscip Rev Syst Biol Med, Nov. 2009; 1(3): 359-371, John Wiley & Sons, Hoboken, NJ.
Delevoye, C et al., "AP-1 and KIF13A coordinate endosomal sorting and positioning during melanosome biogenesis," J. Cell Biol., Oct. 2009; 187: 247-264, Rockefeller University Press, New York, NY.
Deneka, M, et al., "Regulation of membrane transport by rab GTPases," Crit Rev Biochem Mol Biol, Jan. 2003; 38(2): 121-142, Informa Healthcare, London, England.
Murase, D et al., "Autophagy has a significant role in determining skin color by regulating melanosome degradation in keratinocytes," J Investigative Dermatology 133(10):2416-2424; Oct. 2013; published online May 9, 2013; Nature Publishing Group, New York, NY.

\* cited by examiner

Fig. 3
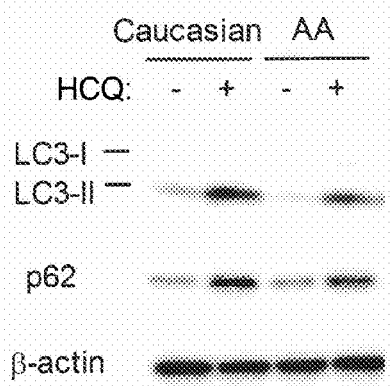
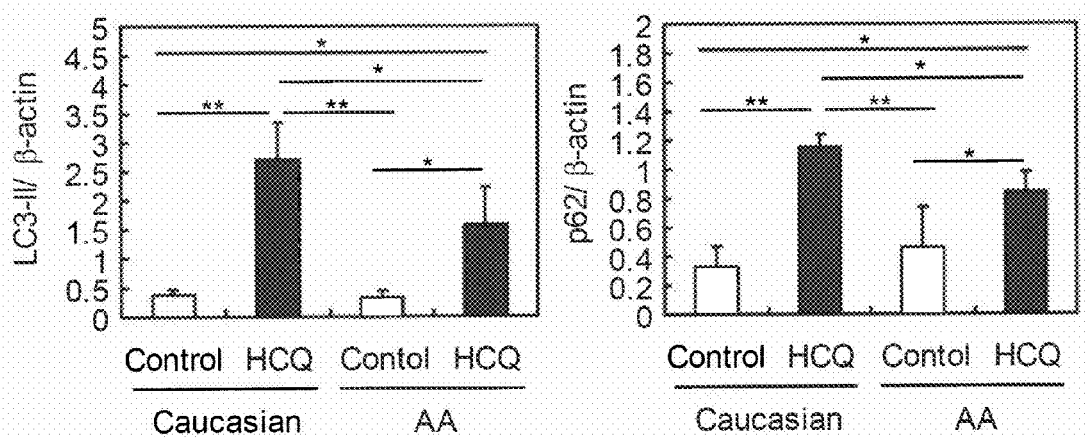

Fig. 5
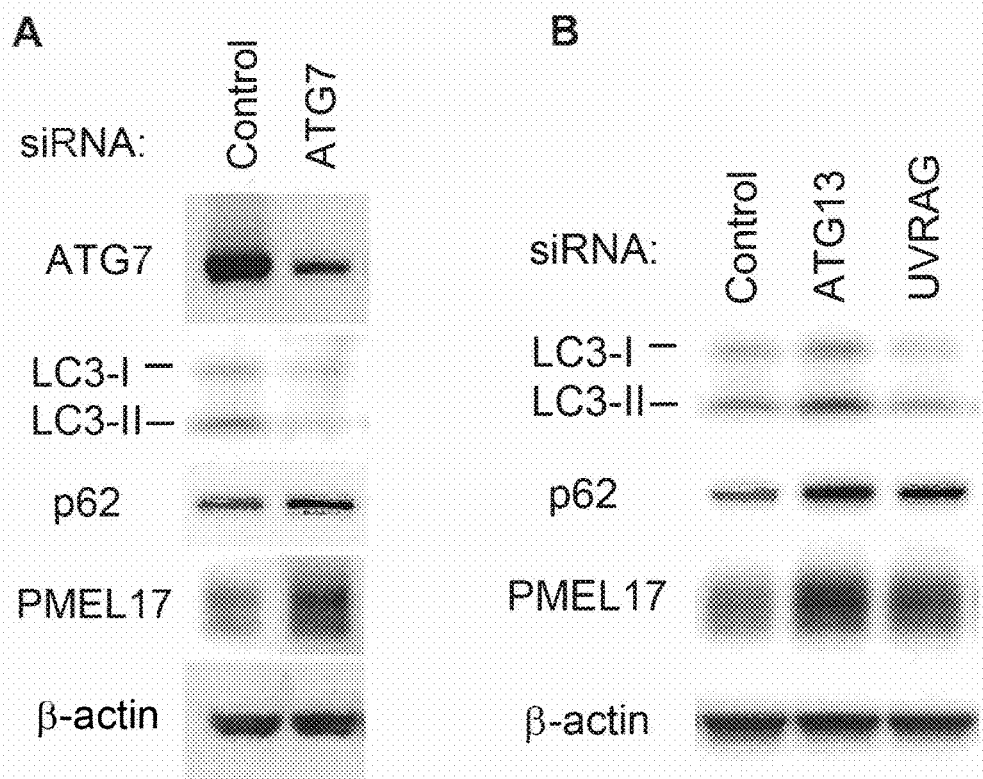
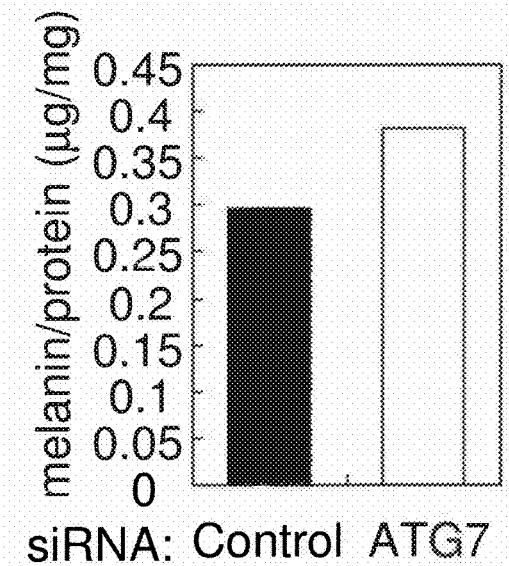

Fig. 8
A
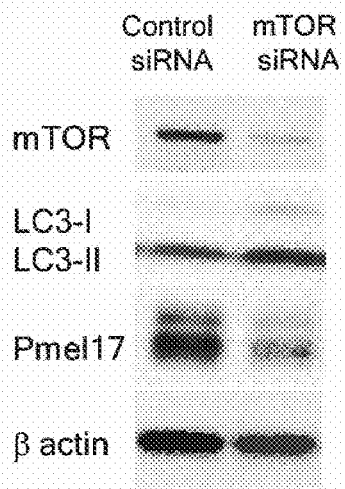
B
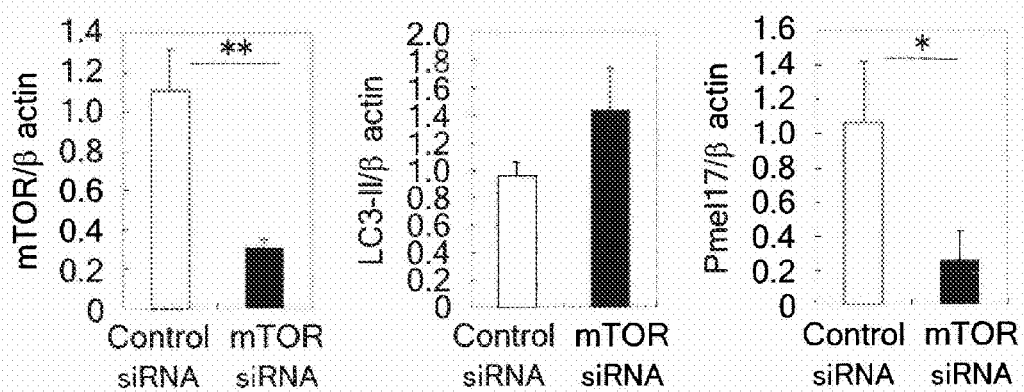

FACTORS CONTROLLING SKIN AND HAIR COLOR

CROSS-REFERENCE TO RELATED PATENT APPLICATION

The present patent application claims the benefit of U.S. Provisional Patent Application No. 61/639,489 filed on Apr. 27, 2012; the entire contents of which are incorporated herein by reference.

FIELD OF THE INVENTION

The present invention relates to regulation of the amount of melanin in keratinocytes, and the control of skin or hair color.

BACKGROUND OF THE INVENTION

Various factors for determining skin or hair color have been reported. Among others, the amount or quality of melanin existing in the epidermis is considered to greatly contribute to skin or hair color. Specifically, it is said that melanin produced in an organelle known as melanosome in a pigment cell (melanocyte) is transferred to keratinocytes in the epidermis or follicle and is then spread over the epidermis and hair as a whole, and that formation of skin or hair color is significantly influenced by such movement of melanin. Such melanin generated by melanocytes has been long known as a factor associated with the skin or hair color of individuals.

Melanocyte, which is a cell associated with the biosynthesis of melanin, contains a melanosome which is a unique lysosome-related organelle derived from endosome. In this melanosome, melanin is synthesized via a catalytic pathway having tyrosine as a precursor. Such a melanosome receives various gene products mainly sorted from trans-Golgi network, and as a result, it has properties shared by lysosome (e.g. internal low pH condition). Nevertheless, structural proteins including a series of melanin synthetases and the related tyrosinase, dopachrome tautomerase and Pmel-17 (GP100) are transferred only to the melanosome, and as a result, the melanosome has a specific property of synthesizing melanin. In the process of generation of skin color, a pigmented melanosome becomes matured as a result of control by various membrane transport factors such as Rab family members, and subsequently, the matured melanosome is transferred to a dendrite and is then transferred to keratinocytes adjacent thereto.

Conventional skin lightening agents have been developed, while mainly targeting generation of melanin in melanocytes. In Non-Patent Document 1, for example, ascorbic acid, arbutin, Kojic acid and the like have been reported as skin lightening agents having an action to inhibit the enzymatic activity of tyrosinase, an enzyme involved in the conversion of tyrosine, which is a melanin precursor, to melanin, so as to suppress generation of melanin.

On the other hand, it has also been reported that a difference is found in the mode or the maturation state of melanin in keratinocytes, according to a difference in skin color (Non-Patent Document 2). That is to say, it is considered that the dynamics of melanin in keratinocytes would play a certain role for determining skin color. According to previous reports, it has been suggested that a receptor molecule PAR-2 be associated with uptake of melanin into keratinocytes (phagocytosis), and that skin color be controlled by regulating such activity (Non-Patent Documents 3 to 8). Moreover, it has also been suggested that protein molecules Dynein or Dynactin be associated with localization of melanin, which has been transferred into keratinocytes, in the keratinocytes (Non-Patent Documents 9 and 10). Furthermore, it has also been suggested that MyoX, a protein molecule involved in formation of a cell structure known as Filopodia, be associated with the transport of melanin from melanocytes to keratinocytes, and from keratinocytes to keratinocytes (Non-Patent Document 11). However, mechanisms regarding the uptake of melanin generated in melanocytes (melanosomes) by keratinocytes, transport, and metabolism have not yet been sufficiently elucidated, and the role of melanin for skin color has not been verified, either.

Recently, as a result of studies using keratinocytes derived from different ethnic groups, it has been suggested that, in terms of the metabolic capacity of melanin taken up, there be a difference among ethnic groups (Non-Patent Document 12). Non-Patent Document 12 reports that melanin is easily degraded in epidermal cells derived from a Caucasian subject, using an evaluation system in which a fluorescent substance-labeled melanin is taken up into epidermal cells and the disappearance of fluorescence in the epidermal cells is then analyzed. However, this document does not refer to any mechanisms contributing to degradation or specific factors.

Autophagy generally means a process in which an intracellular substance such as an organelle is transferred into a lysosome and is then degraded (Non-Patent Documents 13 to 15). It has been known that autophagy includes several types. Among such types, a main pathway, which has been studied most intensively, is macroautophagy. In general, the term "autophagy" indicates such macroautophagy. Autophagy is induced by: various physiological stress such as fasting, hypoxia, energy depletion, endoplasmic reticulum stress, or high temperature; hormonal stimulation; drugs (rapamycin, fluspirilene, trifluoperazine, pimozide, nicardipine, niguldipine, loperamide, amiodarone, verapamil, minoxidil, clonidine, etc.); immune signaling; infection with bacteria, virus and parasite; and disease such as acute pancreatitis or heart disease. Since autophagy-related phenomena have been observed in a wide range of species including yeasts and mammals, autophagy is considered to play an extremely important role for organisms. In fact, it has been reported so far that autophagy is involved in cancer, neurodegenerative disease, inflammation, immunization, aging, and the like (Non-Patent Document 16).

Autophagy consists of a series of processes caused via a special organelle known as an autophagosome. In the autophagic pathway, an isolation membrane or a vesicle called phagophore is first generated in a cytoplasm. The phagophore gradually elongates and then encloses a portion of the cytoplasm, so as to form an autophagosome, which is a sac-like structure having a double membrane. Subsequently, the outer membrane of the autophagosome is fused with a lysosome to form an autolysosome, and in the autolysosome, the enclosed substance is degraded together with the inner membrane of the autophagosome. The degradation product generated as a result of autophagy is reused in a cell. The autophagic pathway is mediated by a plurality of steps such as the generation and elongation of phagophores, formation of autophagosomes, the fusion of autophagosomes with lysosomes, and formation of autolysosomes and degradation of the internal substance, and further, many factors are involved in each step. Main factors are proteins involved in the formation of phagophores and autophagosomes, which are collectively referred to as ATG (Autophagy-related proteins). To date, 30 or more ATGs have been reported (Non-Patent Document 11).

However, it has not been known so far that autophagy is associated with the dynamics of melanin in keratinocytes, such as the uptake, accumulation and degradation of melanin.

CITATION LIST

Non-Patent Document

[Non-Patent Document 1] Bihaku Senryaku (Nankodo Co., Ltd.) IV., *Bihakuzai no Yakuri to Rinsho*, pp. 95-116
[Non-Patent Document 2] Thong et al. (2003) Br J Dermatol 149: 498-505
[Non-Patent Document 3] Lin et al. (2008) Pigment Cell Melanoma Res 21: 172-183
[Non-Patent Document 4] Babiarz-Magee et al. (2004) Pigment Cell Res 17: 241-251
[Non-Patent Document 5] Seiberg et al. (2000) J Invest Dermatol 115: 162-167
[Non-Patent Document 6] Seiberg et al. (2000) Exp Cell Res 25: 25-32
[Non-Patent Document 7] Seiberg (2001) Pigment Cell Res 14: 236-242
[Non-Patent Document 8] Paine et al. (2001) J Invest Dermatol 116: 587-595
[Non-Patent Document 9] Byers et al. (2003) J Invest Dermatol 121: 813-820
[Non-Patent Document 10] Byers et al. (2007) J Invest Dermatol 127: 1736-1744
[Non-Patent Document 11] Singh et al. (2010) FASEB J 24: 3756-3769
[Non-Patent Document 12] Ebanks et al. (2011) J Invest Dermatol 131: 1226-1233
[Non-Patent Document 13] Levine and Kroemer (2008) Cell 132: 27-42
[Non-Patent Document 14] Mizushima et al. (2008) Nature 451: 1069-1075
[Non-Patent Document 15] Rubinsztein (2006) Nature 443: 780-786
[Non-Patent Document 16] Mizushima et al. (2010) Cell 140: 313-326
[Non-Patent Document 17] Mizushima et al. (2007) Autophagy 3: 542-545
[Non-Patent Document 18] Kirkin et al. (2009) Mol Cell: 505-516

SUMMARY OF THE INVENTION

In one aspect, the present invention provides a method for evaluating or selecting an agent for regulating the amount of melanin in a keratinocyte, comprising:
administering a test substance to a cell;
measuring autophagic activity in the cell; and
evaluating an action of the test substance to regulate the amount of melanin, based on a result of the measurement.

In another aspect, the present invention provides a method for evaluating or selecting an agent for controlling skin or hair color, comprising:
administering a test substance to a cell;
measuring autophagic activity in the cell; and
evaluating an action of the test substance to control skin or hair color, based on a result of the measurement.

In a further aspect, the present invention provides a method for regulating the amount of melanin in a keratinocyte, comprising regulating autophagic activity in a keratinocyte, wherein regulation of the amount of melanin is desired in the keratinocyte.

In a further aspect, the present invention provides a method for controlling the skin or hair color of a subject, comprising regulating autophagic activity in the keratinocyte of a subject, wherein the subject desires to control skin or hair color.

BRIEF DESCRIPTION OF THE DRAWINGS

FIG. 3 shows a difference in autophagic activity between races having different skin colors. A: Western blotting analysis; B: quantitative analysis on the expression of p62 and LC3 based on the results of Western blotting. Data indicated with a mean±SD, and **: $p<0.01$; *: $p<0.05$ (ANOVA, Holm test);

FIG. 5 shows an increase in accumulation of melanosomes due to suppression of the expression of autophagy-related factors. A and B: Western blotting analyses; C: melanin accumulation in a cell in which ATG7 expression is suppressed;

FIG. 8 shows the influence of suppression of the expression of the autophagy-suppressing factor mTOR on autophagy and accumulation of melanosomes. A: Western blotting analysis; B: quantitative analysis based on the results of Western blotting. Data indicated with a mean±SD (N=3 each), and **: $p<0.01$; *: $p<0.05$ (ANOVA, Holm test);

DETAILED DESCRIPTION OF THE INVENTION

Figure 1:
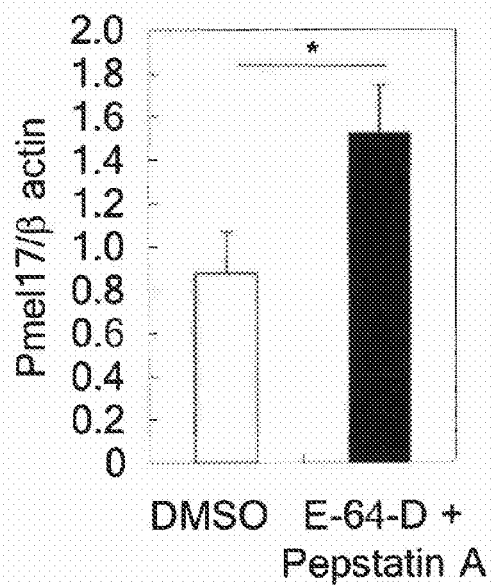
FIG. 1 shows melanin accumulation due to inhibition of lysosomes. A: Western blotting analysis; B: quantitative analysis based on the results of Western blotting. Data indicated with a mean±SD (N=3 each), and *: $p<0.05$ (ANOVA, Holm test)

The present invention relates to a factor associated with regulation of the amount of melanin in keratinocytes and the control of skin or hair color. Moreover, the present invention also relates to a method for regulating the amount of melanin in keratinocytes using the above described factor, a method for controlling skin or hair color, and a method for evaluating or selecting an agent for regulating the amount of melanin in keratinocytes or an agent for controlling skin or hair color, using the above described factor.

The present inventors searched for a factor associated with regulation of the amount of melanin in keratinocytes. As a result, the inventors confirmed that autophagic activity is associated with the amount of melanin in keratinocytes, and that there is a high correlation between autophagic activity and skin color. From these results, the present inventors have found that the amount of melanin in keratinocytes or skin or hair color can be controlled by using autophagic activity.

According to the present invention, skin or hair color can be controlled by regulating the amount of melanin in keratinocytes. In addition, according to the present invention, a material capable of controlling skin or hair color can be evaluated or selected using autophagic activity as an indicator, so that agents for controlling skin or hair color, such as a skin lightening agent, a skin-tanning agent, a hair coloring or bleaching agent, or a hair dye, can be developed.

The term "autophagic activity" is used in the present specification to mean individual steps in the autophagic pathway which include activities such as generation of phagophores, the elongation or growth of phagophores, formation of autophagosomes, the fusion of autophagosomes with lysosomes, formation of autolysosomes, and degradation of a substance in the inside of autolysosomes.

Autophagic activity is reflected, for example, in the expression or activity of an autophagy-related gene or a molecule encoded by the gene. Thus, autophagic activity can be measured by detecting or determining such expression or activity. The expression or activity of an autophagy-related gene or a molecule encoded thereby can be measured by any given analysis method commonly used in the present technical field. Examples of such a gene expression analysis method include dot blotting, Northern blotting, an RNase protection assay, a reporter assay using luciferase or the like, RT-PCR, and DNA microarray. Examples of a method for analyzing or quantifying the expression or activity of a protein encoded by the aforementioned gene include Western blotting, an immunostaining method, a fluorescent staining method, ELISA, and a binding assay.

The term "autophagy-related gene" may be used in the present specification to mean a gene encoding a protein associated with individual steps in the autophagic pathway, such as generation of phagophores, the elongation or growth of phagophores, formation of autophagosomes, the fusion of autophagosomes with lysosomes, formation of autolysosomes, and degradation of a substance in the inside of autolysosomes. Moreover, the term "molecule encoded by the autophagy-related gene" may be used in the present specification to mean a protein and mRNA, which are encoded by the above described gene associated with individual steps in the autophagic pathway.

Examples of a molecule associated with generation of phagophores in mammalian autophagy include ATG1 (or ULK1 or ULK2), ATG13, ATG17, ATG29, ATG31, ATG101, FIP200, VPS34, VPS15 (or p150), ATG6 (or VPS30 or Beclin1), ATG14, Ambra1, ATG2, ATG9, ATG18 (or WIPI1-4), DFVP1, and VMP1. Among these molecules, ATG1 (or ULK1 or ULK2), ATG13, ATG17, ATG29, ATG31, ATG101, and FIP200 are considered to be associated, as ULK/Atg1 complexes, with the initial formation of phagophores (Non-Patent Document 16). On the other hand, VPS34, VPS15, ATG6, ATG14, and Ambra1 act as Class III PI3-kinase complexes, and generate PI(3)P (phosphatidylinositol triphosphate) mainly on the endoplasmic reticulum (Non-Patent Document 16).

Examples of a molecule associated with the growth of phagophores and formation of autophagosomes include ATG5, ATG7, ATG10, ATG12, ATG16 (or ATG16L1), ATG3, ATG4 (or ATG4A-D), ATG8 (or LC3, GATE-16 or GABARAP), and p62. Among these molecules, ATG5, ATG7, ATG10, ATG12, and ATG16 form an Atg12-conjugation system. This system is present outside of phagophores, and is considered to be important for elongation of phagophores (Non-Patent Document 16). On the other hand, LC3, ATG3, ATG4, and ATG7 form an LC3/Atg8-conjugation system. It is considered that this system is involved in elongation of phagophores and the closure of the membrane (Non-Patent Document 16). LC-3 is a mammalian homolog of yeast Atg8, and it includes LC3-I and LC3-II. Of these, LC3-II is formed by the covalent binding of phosphatidyl ethanolamine to cytoplasmic localization-type LC3-I, and it is thereby localized on the autophagosomal membrane. Since the amount of LC3-II is proportional to the number of autophagosomes, LC3-II has been known as an indicator of autophagy (Non-Patent Document 17). For example, an autophagy inhibitor such as hydroxychloroquine or a protein degradation inhibitor such as E-64-D or pepstatin A is added, and the amount of an LC3-II protein accumulated is then measured, so that autophagic activity can be quantitatively evaluated. Otherwise, the amount of the LC3-II protein is detected in each sample, and LC3-II is then used in combination with another known autophagy marker such as p62, so as to evaluate autophagic activity (Non-Patent Document 17). Such p62 is a protein which is localized in an autophagosome-forming site and interacts with LC3, and this protein has a function of recruiting an autophagy-targeted protein to autophagosomes. In addition, p62 has been known as an autophagy-selective substrate, as in the case of Nbr1 (Non-Patent Document 18).

Examples of a molecule associated with the fusion of autophagosomes with lysosomes include UVRAG (or VPS38) and RAB7. UVRAG has been known as a molecule which promotes the fusion process of autophagosomes with lysosomes.

In the present specification, the "autophagy-related gene or a molecule encoded by the gene" preferably does not include genes selected from the group consisting of ATG7, RAB11A, CLIP-170, Rubicon and RAB7B, and molecules encoded by these genes.

Examples of the "autophagy-related gene or a molecule encoded by the gene" will be shown in Table 1 below. The below-mentioned examples are genes and proteins registered in a known database. However, the association of these genes and molecules with the dynamics of melanin in keratinocytes has not previously been known.

TABLE 1

| Gene | Gene ID (NCBI) | Accession No. | Proteins coded | DB code No. of proteins |
| --- | --- | --- | --- | --- |
| ATG7 | 10533 | NM_006395.2 | ATG7 | NP_006386.1 |
| ATG5 | 9474 | NM_004849.2 | ATG5 | NP_004840.1 |
| ULK1 | 8408 | NM_003565.1 | ULK1 | NP_003556.1 |

TABLE 1-continued

| Gene | Gene ID (NCBI) | Accession No. | Proteins coded | DB code No. of proteins |
|---|---|---|---|---|
| ULK2 | 9706 | NM_014683.3 | ULK2 | NP_055498.3 |
| KIAA0652 | 9776 | NM_014741.3 | ATG13 | NP_055556.2 |
| RB1CC1 | 9821 | NM_014781.4 | FIP200 | NP_055596.3 |
| C12orf44 | 60673 | NM_021934.4 | ATG101 | NP_068753.2 |
| PIK3C3 | 5289 | NM_002647.2 | VPS34 | NP_002638.2 |
| PIK3R4 | 30849 | NM_014602.2 | p150 | NP_055417.1 |
| BECN1 | 8678 | NM_003766.3 | Beclin1 | NP_003757.1 |
| KIAA0831 | 22863 | NM_014924.3 | ATG14 | NP_055739.2 |
| AMBRA1 | 55626 | NM_017749.2 | AMBRA1 | NP_060219.2 |
| ATG12 | 9140 | NM_004707.2 | ATG12 | NP_004698.2 |
| ATG2A | 23130 | NM_015104.1 | ATG2A | NP_055919.1 |
| ATG2B | 55102 | NM_018036.5 | ATG2B | NP_060506.5 |
| ATG9A | 79065 | NM_001077198.1 | ATG9A | NP_001070666.1 |
| ATG9B | 285973 | NM_173681.4 | ATG9B | NP_775952.3 |
| WIPI1 | 55062 | NM_017983.5 | WIPI1 | NP_060453.3 |
| WIPI2 | 26100 | NM_015610.3 | WIPI2 | NP_056425.1 |
| WDR45L | 56270 | NM_019613.3 | WIPI3 | NP_062559.2 |
| WDR45 | 11152 | NM_001029896.1 | WIPI4 | NP_001025067.1 |
| ZFYVE1 | 53349 | NM_021260.1 | DFCP1 | NP_067083.1 |
| TMEM49 | 81671 | NM_030938.3 | VMP1 | NP_112200.2 |
| ATG10 | 83734 | NM_031482.4 | ATG10 | NP_113670.1 |
| ATG16L1 | 55054 | NM_030803.6 | ATG16L1 | NP_110430.5 |
| MAP1LC3A | 84557 | NM_181509.1 | LC3 | NP_852610.1 |
| ATG4A | 115201 | NM_052936.2 | ATG4A | NP_443168.2 |
| ATG4B | 23192 | NM_013325.4 | ATG4B | NP_037457.3 |
| ATG4C | 84938 | NM_032852.2 | ATG4C | NP_116241.2 |
| ATG4D | 84971 | NM_032885.4 | ATG4D | NP_116274.3 |
| ATG3 | 64422 | NM_022488.3 | ATG3 | NP_071933.2 |
| UVRAG | 7405 | NM_003369.3 | UVRAG | NP_003360.2 |
| SQSTM1 | 8878 | NM_001142298.1 | SQSTM1 (p62) | NP_001135770.1 |

In the present specification, the autophagy-related gene or a molecule encoded by the gene may include their homologs. For example, in the present invention, instead of the genes or proteins shown in Table 1, their homologs may be used. In the present specification, a gene or protein, which has high sequence identity with another certain gene or protein and has functions equivalent to those of the certain gene or protein, and preferably shares its evolutionary origin with the certain gene or protein, is referred to as a "homolog" of the certain gene or protein. For instance, a gene, which has identity of 60% or more, and preferably 80% or more at a nucleotide sequence level with a certain autophagy-related gene, and which encodes a protein associated with individual steps in the autophagic pathway, such as generation of phagophores, the elongation or growth of phagophores, formation of autophagosomes, the fusion of autophagosomes with lysosomes, formation of autolysosomes, and degradation of a substance in the inside of autolysosomes, and which is preferably derived from the same evolutionary origin as that of the certain autophagy-related gene, is a homolog of the above described autophagy-related gene. Moreover, for example, a protein, which is encoded by a homolog gene of the above described autophagy-related gene and which is associated with the steps in the autophagic pathway with which the protein encoded by the autophagy-related gene is associated, is a homolog of the protein encoded by the autophagy-related gene.

The term "identity" regarding an amino acid sequence or a nucleotide sequence is used in the present specification to mean the percentage (%) of the number of positions, in which identical amino acid residues or nucleotides are present in two amino acid sequences or nucleotide sequences, to the number of the full-length amino acid residues or nucleotides, when the two amino acid sequences or nucleotide sequences are aligned (alignment). Specifically, the identity used herein means a value, which is obtained by calculating according to the Lipman-Pearson method (Science, 227, 1435, 1985), and then conducting analysis using the homology analysis (Search homology) program of gene information processing software Genetyx-Win (Ver. 5.1.1; Software Development), in which the Unit size to compare (ktup) is set at 2.

In the present invention, at least one of the autophagy-related gene or a molecule encoded by the gene may be used. In other words, the gene or the molecule may be used singly, but they may also be used in combination of any given two or more genes or molecules. For example, the autophagy-related gene or a molecule encoded by the gene, which is used in the present invention, may be at least one of autophagy-related genes or molecules encoded by the genes, selected from the group consisting of the genes listed in Table 1, and mRNAs and proteins encoded by the genes. More specifically, the genes, or mRNAs or proteins encoded thereby, as listed in Table 1, may be used singly in the present invention, or any given two or more of the genes may be used in combination, or mRNAs encoded by any given two or more of the genes may be used in combination, proteins encoded by any given two or more of the genes may be used in combination, or any given two or more combinations selected from such genes, mRNAs and proteins may also be used.

Figure 2:
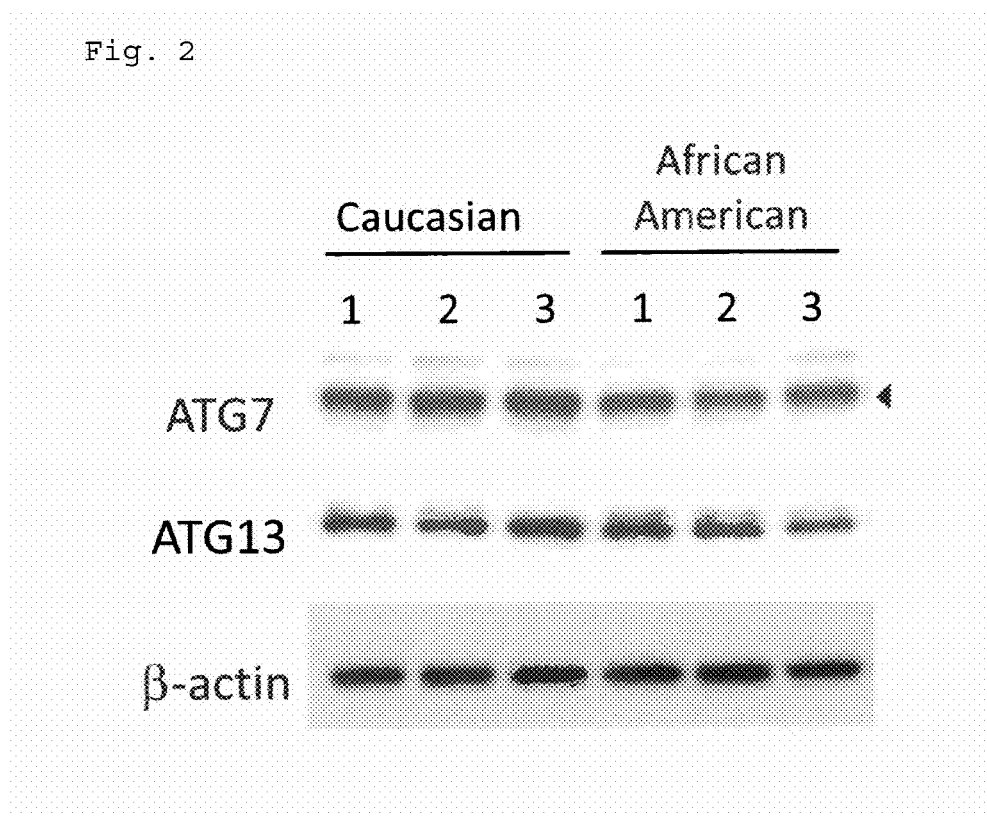
FIG. 2 shows a difference in the expression of autophagy-related factors between races having different skin colors.
Figure 4:
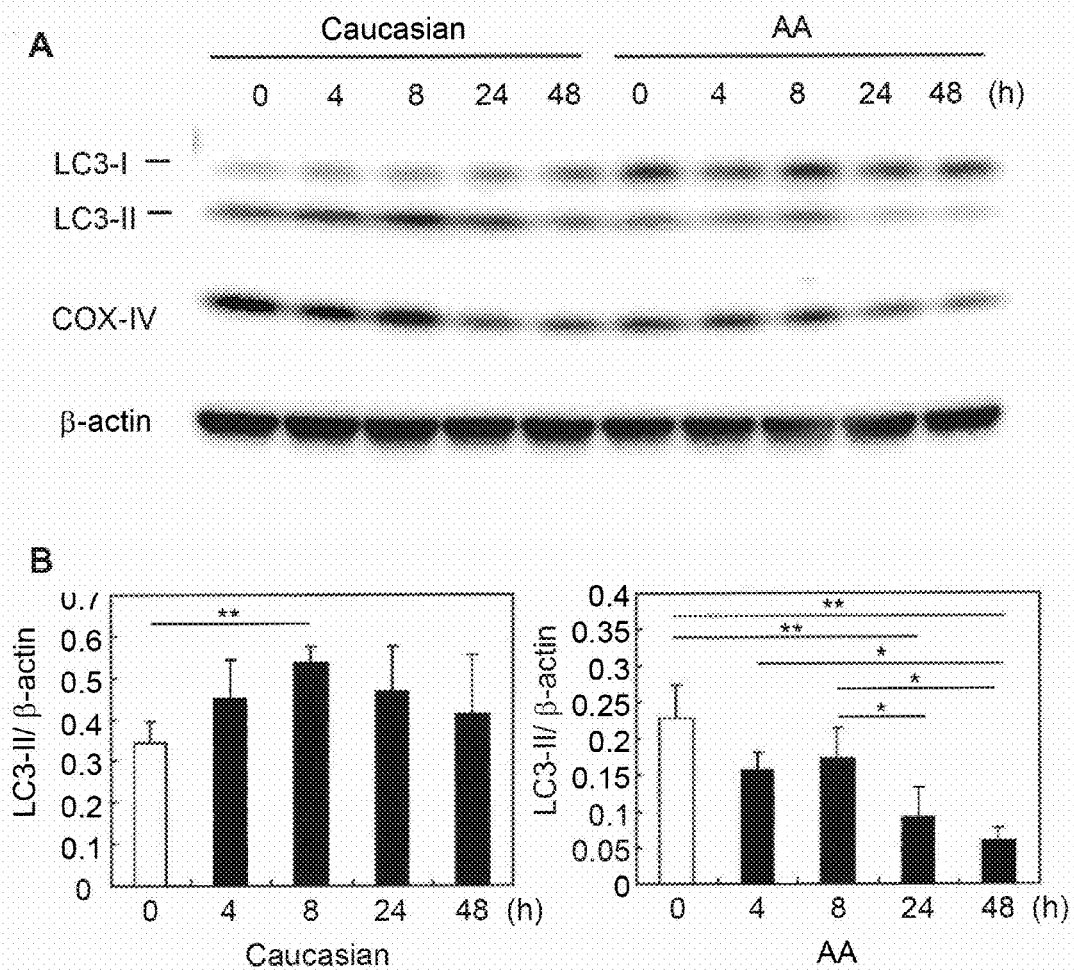
FIG. 4 shows a difference in autophagic activity after uptake of melanosomes between races having different skin colors. A: Western blotting analysis; B: quantitative analysis on the expression based on the results of Western blotting. Data indicated with a mean±SD, and **: $p<0.01$; *: $p<0.05$ (ANOVA, Holm test)
Figure 9:
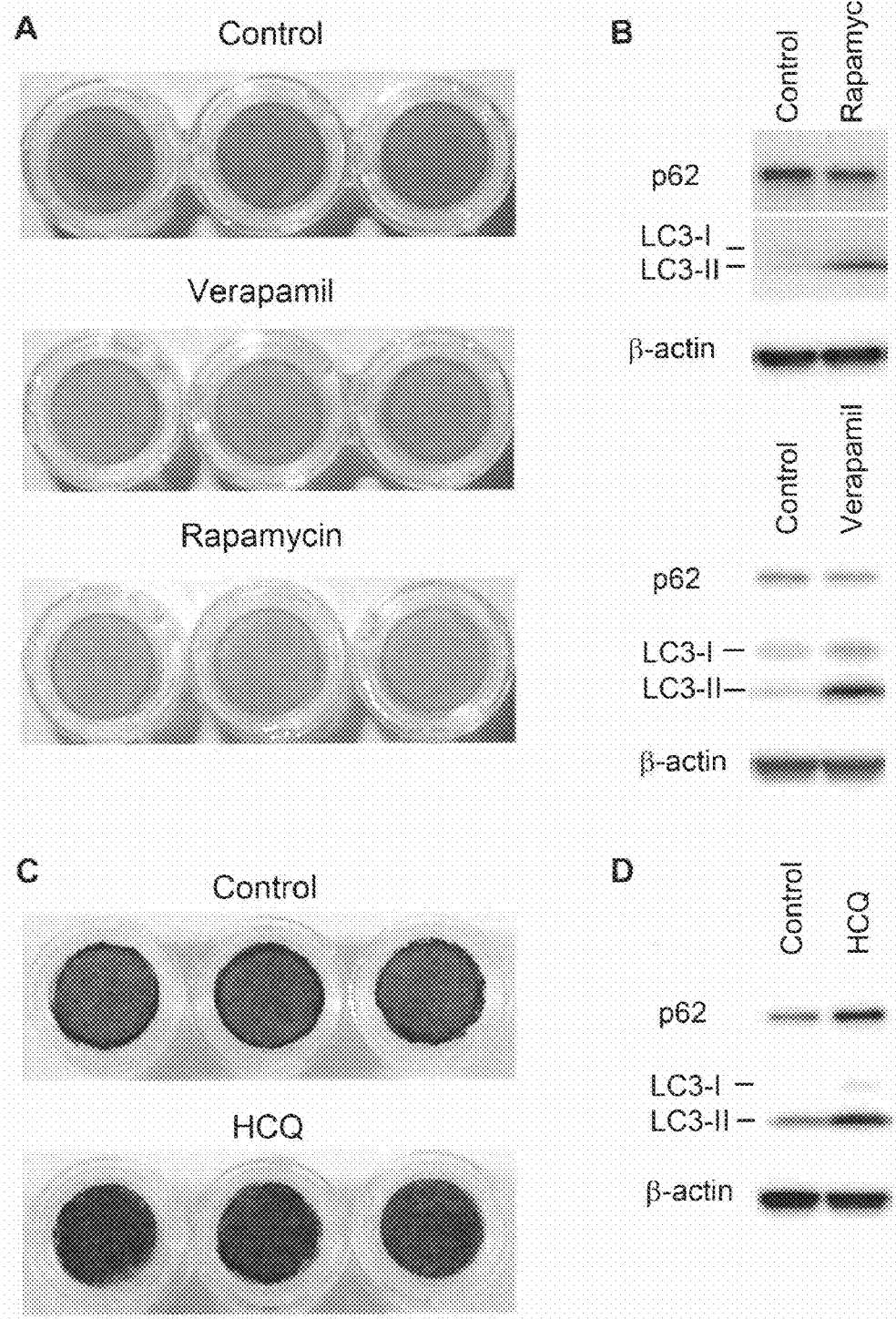
FIG. 9 shows the influence of autophagy regulation on the content of melanin in keratinocytes. (A) Photographs and (B) Western blotting analysis of cultures after completion of the culture in the presence of an autophagy inducer. (C) Photographs and (D) Western blotting analysis (D) of cultures after completion of the culture in the presence of an autophagy inhibitor.
Figure 10:
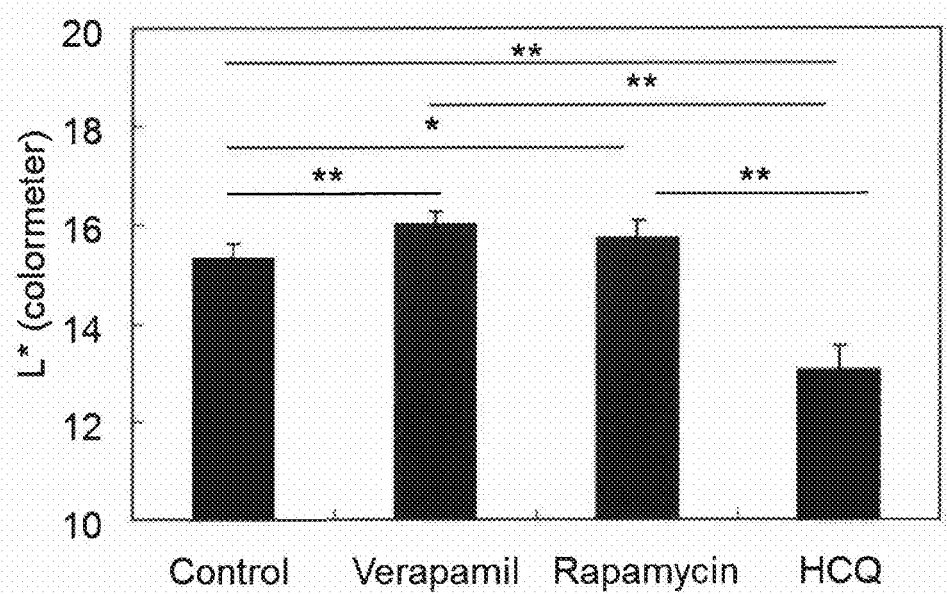
FIG. 10 shows the lightness (L* value) of the skin cultured with an autophagy-regulating agent. Data indicated with a mean±SD (N=3 each), and **: $p<0.01$; *: $p<0.05$ (ANOVA, Holm test)

As described in Examples later, autophagic activity in keratinocytes derived from the skin of a person having light skin color was higher than autophagic activity in keratinocytes derived from the skin of a person having dark skin color (FIG. 2 to 4). Also, as described in Examples later, degradation of melanosomes after being taken up into keratinocytes was suppressed by inhibition of the expression of the autophagy-related proteins ATG7, ATG13, ATG5, RAB11A and UVRAG (FIG. 5 to 8). On the other hand, the cultured skin models became lightened or darkened by the use of an autophagy inducer or inhibitor (FIGS. 9 and 10). That is to say, it was demonstrated that autophagic activity contributes to regulation of the amount of melanin in keratinocytes or the control of skin or hair color.

The dynamics of melanin in keratinocytes, such as the uptake, transport, localization, accumulation, elimination and degradation of melanin transferred from melanocytes, are deeply associated with the amount and distribution of melanin in an epidermal layer of the skin that is mainly constituted with keratinocytes, hair matrix cells in the follicle, or cortex cells constituting a shaft, and more broadly speaking, the dynamics of melanin in keratinocytes have an influence on skin and hair colors.

The amount of melanin in keratinocytes can be regulated by changing autophagic activity in keratinocytes, and thereby, the amount and distribution of melanin in an epidermal layer of the skin, hair matrix cells in the follicle, and further, cortex cells constituting a shaft can be regulated, so that skin and hair colors can be controlled.

For instance, a decrease in autophagic activity in keratinocytes increases the amount of melanin in the keratinocytes, so as to darken the color of the cells. On the contrary, the amount of melanin in keratinocytes is decreased by enhancing autophagic activity in the keratinocytes, so that the color of the cells becomes lightened. Hence, skin and hair colors become lightened by enhancing autophagic activity in keratinocytes. On the contrary, skin and hair colors become darkened by decreasing autophagic activity in keratinocytes.

As an example of a means for changing the autophagic activity of cells, there is applied a method of changing the expression or activity of the above described autophagy-related gene or a molecule encoded by the gene in the cells.

For example, among the above described autophagy-related genes and molecules encoded thereby, a decrease in the expression of genes and molecules associated with activation of autophagy in keratinocytes leads to a decrease in autophagic activity. As a result, it increases the amount of melanin in keratinocytes and darkens the color of the cells. On the contrary, since autophagic activity is enhanced by an increase in the expression of these genes and molecules, the amount of melanin in keratinocytes is decreased, and the color of the cells becomes lightened.

Accordingly, skin and hair colors become lightened by increasing the expression or activity of a gene or molecule associated with activation of autophagy in keratinocytes. In contrast, skin and hair colors become darkened by decreasing the expression or activity of the aforementioned gene or molecule.

Moreover, for example, among the above described autophagy-related genes and molecules encoded thereby, an increase in the expression of genes and molecules associated with suppression of autophagic activity in keratinocytes decreases autophagic activity. As a result, it increases the amount of melanin in keratinocytes and darkens the color of the cells. On the contrary, since autophagic activity is enhanced by a decrease in the expression of these genes and molecules, the amount of melanin in keratinocytes is decreased and the color of the cells becomes lightened.

Accordingly, skin and hair colors become lightened by decreasing the expression or activity of a gene or molecule associated with suppression of autophagic activity in keratinocytes. In contrast, skin and hair colors become darkened by increasing the expression or activity of the aforementioned gene or molecule.

A gene associated with activation of autophagy, a gene associated with suppression of autophagic activity, and molecules encoded by these genes can be identified by examining the influence of the expression of such genes or molecules on autophagic activity according to ordinary means.

For example, an autophagy inducer or autophagy inhibitor having an unknown action mechanism is administered to promote or reduce autophagic activity. Then, genes or molecules whose expression is changed by the administration of the agent are determined. Thereafter, a change in autophagic activity is examined when such genes or molecules are overexpressed or the expression thereof is suppressed, so as to identify a gene or a molecule associated with activation of autophagy or suppression of the autophagic activity. Alternatively, in the case of genes or molecules whose association with autophagy has been known, it may be sufficient to only examine a change in autophagic activity when such genes or molecules are overexpressed or the expression thereof is suppressed.

LC3 (e.g. LC3-I and LC3-II), p62, COX-IV, and ATG5, ATG13, RAB11A and UVRAG genes, and mRNAs and proteins encoded thereby, which will be described in Examples later, are given as examples of the genes and molecules associated with activation of autophagy or suppression of the autophagic activity. Moreover, the genes or proteins listed in Table 1 above, or their homologs, are also given as examples of the genes and molecules associated with activation of autophagy or suppression of the autophagic activity.

By changing the expression or activity of the above described autophagy-related gene or a molecule encoded by the gene, the amount of melanin in keratinocytes can be regulated, and skin or hair color can be controlled. In other words, the above described autophagy-related gene or a molecule encoded by the gene can be used to regulate the amount of melanin in keratinocytes or to control skin or hair color. Otherwise, the above described autophagy-related gene or a molecule encoded by the gene can be used to produce an agent for regulating the amount of melanin in keratinocytes or for controlling skin or hair color.

The expression or activity of the autophagy-related gene or a molecule encoded by the gene may be changed by any given means commonly used in the present technical field. With regard to a means for changing the expression of the aforementioned gene or the expression or activity of the aforementioned molecule, examples of a means for changing gene expression include: gene knockdown with the use of antisense oligonucleotide, siRNA or the like; activation of the transcription of a target gene using a specific promoter; introduction of a foreign gene with the use of a vector; and addition of any given substance having an action to change the expression of the gene. Of these means, the addition of any given substance having an action to change the expression of the gene is preferable.

With regard to a vector used for introduction of a gene, examples of a vector used for cultured cells include various gene expression vectors, into which a CMV promoter or an EF1α promoter has been incorporated. Examples of a vector used for cultured cells and tissues include an adenovirus vector, a retrovirus vector, and a lentivirus vector. Procedures for gene introduction using these vectors have been well known to a person skilled in the art. For example, procedures for introduction of a gene into the skin using a lentivirus vector are described in Gene Ther. 2007 April, 14(8): 648-56. Moreover, gene introduction kits comprising these vectors are commercially available. By introducing, into cells, the above described vector into which an autophagy-related gene has been incorporated, the autophagy-related gene is overexpressed in the cells, so that autophagic activity can be changed.

Gene knockdown with siRNA is a means for specifically inhibiting the expression of a target gene by inducing mRNA degradation in a sequence-specific manner based on the mechanism of RNA interference (RNAi). Such siRNA has also been used in the in vivo gene knockdown in various organisms including mammals (see, for example, Song et al., Nature Medicine, 2003, 9: 347-351; McCaffery et al., Nature, 2002, 418: 38-39; Lewis et al., Nature Genetics, 2002, 32: 107-108; Xia et al., Nature Biotech., 2002, 20: 1006-1010). Target-specifically synthesized siRNA is commercially available, and a kit for siRNA transfection can be purchased from many distributers such as QUIAGEN or Takara Bio Inc.

Examples of a molecule encoded by the above described autophagy-related gene include mRNA and polypeptide encoded by the gene. Herein, the description "a change in the expression or activity of a molecule" may be used to mean any given conditions for changing the expression or activity of the molecule as a whole, such as a change in the expression level of the molecule, a change in the degradation rate of the molecule, a change in the activation rate of the molecule, and a change in the inactivation rate of the molecule. The above description "a change in the expression or activity of a molecule" preferably means a change in the expression level of the molecule. Examples of a means for changing the expression or activity of a molecule include: the above described means for changing gene expression; a means for changing the expression of a protein; a means for changing the enzymatic activity of a molecule; a means for changing the interaction of a molecule with a target factor thereof; and a means for changing a signaling pathway on which a molecule acts. Among these means, a means for changing the expression of a gene, a means for changing the expression of a protein, and the like are preferable.

Another example of the means for changing autophagic activity is administration of an autophagy inducer or an autophagy inhibitor, etc. Examples of a known autophagy inducer include mTOR signaling inhibitors having rapamycin as a typical example; and proteasome inhibitors such as fluspirilene, trifluoperazine, pimozide, nicardipine, niguldipine, loperamide, amiodarone, verapamil, minoxidil, clonidine, PP242, or MG-132. Examples of a known autophagy inhibitor include hydroxychloroquine, chloroquine, bafilomycin A1, and PI3 kinase inhibitors such as 3-methyladenine or wortmannin.

Further examples of a means for changing autophagic activity include: activation or suppression of a target factor of the above described autophagy inducer or inhibitor; and activation or suppression of a factor which has an influence on the expression of the autophagy-related genes or molecules encoded by the genes shown in Table 1 above. For example, the aforementioned autophagy inducer rapamycin suppresses the activity of a cellular protein mTOR. mTOR (mammalian target of rapamycin) is a protein discovered as a target of rapamycin, which is one of protein kinases (serine-threonine kinase) involved in intracellular signaling. Also, mTOR has been known to have an action to suppress autophagy induction (Nat Genet. 2004 June; 36(6): 585-95). As described in Example 8 later, by suppressing mTOR, the autophagic activity of cells was increased, and the amount of melanin was decreased.

In the present invention, examples of a subject whose autophagic activity is to be changed include: keratinocytes, which have an ability to express at least one of the above described, natural or genetically modified genes, and in which regulation of the amount of melanin is desired; and a culture, a tissue, an organ, and an animal, which contain the same. The above described keratinocytes are preferably those exist in the skin or follicle, and are more preferably epidermal keratinocytes, hair matrix cells and cortex cells. Preferred examples of the above described culture, tissue and organ containing the keratinocytes include cultured keratinocytes, and epidermal tissues, follicular tissues, skin and the cultures thereof. The above described animals are preferably human or non-human mammals. Examples of such non-human animal include a dog, a cat, a rabbit, a mouse, a rat, a hamster, a guinea pig, a pig, and a horse.

In one aspect, the above described regulation of the amount of melanin or control of skin or hair color according to the present invention can be carried out on the above described keratinocyte, or a culture, a tissue or an organ containing the same, which are used as subjects. The subjects are preferably cultured keratinocytes, cultured skin tissues, cultured epidermis, or cultured follicle. In another aspect, with regard to the above described regulation of the amount of melanin or control of skin or hair color according to the present invention, an animal, which desires the regulation of the amount of melanin in keratinocytes or the control of skin or hair color, may be used as a subject.

In another aspect, the regulation of the amount of melanin or the control of skin or hair color can be non-therapeutically carried out by non-medical workers, preferably such as an aesthetician, a hairdresser, a barber or a trimmer, for cosmetic or aesthetic purpose, for example, for the purpose of skin lightening or tanning, hair coloring (lightening or darkening) or bleaching, returning to natural hair color after bleaching, hair dying, etc. The term "non-therapeutic" is used in the present specification to mean a concept which does not include medical treatments, namely, therapeutic treatments on human bodies.

An exemplary aspect of the present invention is a method for increasing the amount of melanin in a keratinocyte, comprising suppressing autophagic activity in keratinocyte in which an increase in the amount of melanin is desired, so as to increase the amount of melanin in the keratinocyte.

Another exemplary aspect of the present invention is a method for decreasing the amount of melanin in a keratinocyte, comprising enhancing autophagic activity in keratinocytes in which a decrease in the amount of melanin is desired, so as to decrease the amount of melanin in the keratinocyte.

One embodiment of the above described aspects is a method for increasing the amount of melanin in a keratinocyte, comprising suppressing the expression or activity of a gene associated with activation of autophagy or a molecule encoded thereby in a keratinocyte in which an increase in the amount of melanin is desired, so as to increase the amount of melanin in the keratinocyte.

Another embodiment is a method for decreasing the amount of melanin in a keratinocyte, comprising enhancing the expression or activity of a gene associated with activation of autophagy or a molecule encoded thereby in a keratinocyte in which a decrease in the amount of melanin is desired, so as to decrease the amount of melanin in the keratinocyte.

A further embodiment is a method for increasing the amount of melanin in a keratinocyte, comprising enhancing the expression or activity of a gene associated with suppression of autophagic activity or a molecule encoded thereby in a keratinocyte in which an increase in the amount of melanin is desired, so as to increase the amount of melanin in the keratinocyte.

A further embodiment is a method for decreasing the amount of melanin in a keratinocyte, comprising suppressing the expression or activity of a gene associated with suppression of autophagic activity or a molecule encoded thereby in a keratinocyte in which a decrease in the amount of melanin is desired, so as to decrease the amount of melanin in the keratinocyte.

Another exemplary aspect of the present invention is a method for browning or darkening the skin color of a subject, comprising suppressing autophagic activity in the skin keratinocyte of the subject who desires to brown or darken the skin color, so as to increase the amount of melanin in the keratinocyte. This method enables the tanning of the skin, for example.

Another exemplary aspect of the present invention is a method for lightening the skin color of a subject, comprising enhancing autophagic activity in the skin keratinocyte of the subject who desires to lighten the skin color, so as to decrease the amount of melanin in the keratinocyte. This method enables skin lightening, for example.

One embodiment of the above described aspects is a method for browning or darkening the skin color of a subject, comprising suppressing the expression or activity of a gene associated with activation of autophagy or a molecule encoded thereby in the skin keratinocyte of the subject who desires to brown or darken the skin color, so as to increase the amount of melanin in the keratinocyte. This method enables the tanning of the skin, for example.

Another embodiment is a method for lightening the skin color of a subject, comprising enhancing the expression or activity of a gene associated with activation of autophagy or a molecule encoded thereby in the skin keratinocyte of the subject who desires to lighten the skin color, so as to decrease the amount of melanin in the keratinocyte. This method enables skin lightening, for example.

A further aspect is a method for browning or darkening the skin color of a subject, comprising enhancing the expression or activity of a gene associated with suppression of autophagic activity or a molecule encoded thereby in the skin keratinocyte of the subject who desires to brown or darken the skin color, so as to increase the amount of melanin in the keratinocyte. This method enables the tanning of the skin, for example.

A further embodiment is a method for lightening the skin color of a subject, comprising suppressing the expression or activity of a gene associated with suppression of autophagic activity or a molecule encoded thereby in the skin keratinocyte of the subject who desires to lighten the skin color, so as to decrease the amount of melanin in the keratinocyte. This method enables skin lightening, for example.

A further exemplary aspect of the present invention is a method for browning or darkening the hair color of a subject, comprising suppressing autophagic activity in the follicular keratinocyte of the subject who desires to brown or darken the hair color, so as to increase the amount of melanin in the keratinocyte. This method enables returning to natural hair color after bleaching, or hair dying, for example.

A further exemplary aspect of the present invention is a method for lightening the hair color of a subject, comprising enhancing autophagic activity in the follicular keratinocyte of the subject who desires to lighten the hair color, so as to decrease the amount of melanin in the keratinocyte. This method enables the lightening or bleaching of hair color, for example.

One embodiment of the above described aspects is a method for browning or darkening the hair color of a subject, comprising suppressing the expression or activity of a gene associated with activation of autophagy or a molecule encoded thereby in the follicular keratinocyte of the subject who desires to brown or darken the hair color, so as to increase the amount of melanin in the keratinocyte. This method enables returning to natural hair color after bleaching, or hair dying, for example.

Another embodiment is a method for lightening the hair color of a subject, comprising enhancing the expression or activity of a gene associated with activation of autophagy or a molecule encoded thereby in the follicular keratinocyte of the subject who desires to lighten the hair color, so as to decrease the amount of melanin in the keratinocyte. This method enables the lightening or bleaching of hair color, for example.

A further embodiment is a method for browning or darkening the hair color of a subject, comprising enhancing the expression or activity of a gene associated with suppression of autophagic activity or a molecule encoded thereby in the follicular keratinocyte of the subject who desires to brown or darken the hair color, so as to increase the amount of melanin in the keratinocyte. This method enables returning to natural hair color after bleaching, or hair dying, for example.

A further embodiment is a method for lightening the hair color of a subject, comprising suppressing the expression or activity of a gene associated with suppression of autophagic activity or a molecule encoded thereby in the follicular keratinocyte of the subject who desires to lighten the hair color, so as to decrease the amount of melanin in the keratinocyte. This method enables the lightening or bleaching of hair color, for example.

A substance which changes autophagic activity is a substance capable of controlling skin or hair color by regulating the amount of melanin in keratinocytes. Accordingly, the present invention also provides: a method for evaluating an action of a substance to regulate the amount of melanin in a keratinocyte or the action of a substance to control skin or hair color; and a method for evaluating or selecting an agent for regulating the amount of melanin in a keratinocyte or an agent for controlling skin or hair color, wherein the above methods utilize autophagic activity.

The method for evaluating or selecting an agent for regulating the amount of melanin in a keratinocyte according to the present invention comprises: administering a test substance to a cell; measuring a change in autophagic activity in the cell; and evaluating an action of the test substance to regulate the amount of melanin, based on a result of the measurement.

The cell to which the test substance is to be administered may be either a natural cell or genetically modified cell, as long as they have autophagic activity. Cultured cells, or cells derived from the cultures of animal tissues or organs, are preferable. Of these, cultured human cells are more preferable. Moreover, the cell is preferably skin cell, more preferably epidermal cell or follicular cell, and even more preferably keratinocyte. Specific examples of preferred cells include human-derived cultured epidermal cells (e.g. normal human epidermal keratinocyte; NHEK) and human tissue-cultured follicular cells.

The type of the test substance may be either a natural product or a synthetic product. Also, it may be any one of a single substance, a composition, and a mixture. The dosage form of a test substance may be any given form, depending on the type of the test substance.

Autophagic activity can be measured, for example, by examining the expression or activity of an autophagy-related gene or a molecule encoded by the gene, or the amount of the molecule in cells. The expression or activity of the above-mentioned gene or a molecule encoded thereby, or the amount of the molecule in cells, can be measured by any given analysis method commonly used in the present technical field. Examples of such a gene expression analysis method include dot blotting, Northern blotting, an RNase protection assay, a reporter assay using luciferase or the like, RT-PCR, and DNA microarray. Examples of a method for analyzing or quantifying the expression or activity of a protein encoded by the aforementioned gene include Western blotting, an immunostaining method, a fluorescent staining method, ELISA, and a binding assay.

A change in autophagic activity by administration of a test substance can be evaluated based on the measured autophagic activity. For instance, autophagic activity is measured before and after administration of a test substance, the measurement values are then quantified as necessary, and a comparison may be then made on the results before and after administration of the test substance. Alternatively, for instance, a test substance administration group, and a test substance non-administration group or a control substance administration group, are measured in terms of autophagic activity, the measurement values are then quantified as necessary, and a comparison may be then made between the administration group and the non-administration group, or between the administration group and the control substance administration group. Further, test substances, each having different concentrations, are administered, autophagic activity is then measured, and a difference in the measurement results due to the concentrations of the test substances may be then examined.

On the basis of the above described measurement results of autophagic activity, the action of a test substance to regulate the amount of melanin in keratinocytes can be evaluated. A test substance evaluated to have an influence on autophagic activity may be determined to be a substance having an action to regulate the amount of melanin in keratinocytes, or the test substance may be selected as an agent for regulating the amount of melanin in keratinocytes which can be used to regulate the amount of melanin in keratinocytes. Accordingly, the method for evaluating or selecting an agent for regulating the amount of melanin according to the present invention may further comprise selecting the test substance as an agent for regulating the amount of melanin in a keratinocyte, based on the evaluation results of the test substance.

For example, a substance which suppresses autophagic activity is selected as an agent for increasing the amount of melanin in keratinocytes. Examples of such a substance include: a substance which suppresses the expression or activity of a gene associated with activation of autophagy or a molecule encoded thereby; and a substance which enhances the expression or activity of a gene associated with suppression of autophagic activity or a molecule encoded thereby. The above-mentioned agent can be used as an agent for browning or darkening skin or hair color, which increases the amount of melanin in keratinocytes so as to brown or darken skin or hair color (e.g. a skin tanning agent, an agent for darkening hair color, an agent for returning bleached hair to natural hair color, a hair dye, etc.).

On the other hand, a substance which enhances autophagic activity is selected as an agent for decreasing the amount of melanin in keratinocytes. Examples of such a substance include: a substance which enhances the expression or activity of a gene associated with activation of autophagy or a molecule encoded thereby; and a substance which suppresses the expression or activity of a gene associated with suppression of autophagic activity or a molecule encoded thereby. The above-mentioned agent can be used as an agent for lightening skin or hair color, which decreases the amount of melanin in keratinocytes so as to lighten skin or hair color (e.g. a skin lightening agent, an agent for lighting or bleaching hair color, etc.).

The present invention further provides a method for selecting an agent for controlling skin or hair color. This method comprises: administering a test substance to a cell; measuring a change in autophagic activity in the cell; and evaluating an action of the test substance to control skin or hair color, based on a result of the measurement. The cell, the test substance, the method for measuring the expression or activity of a gene or a molecule, and the method for evaluating the measurement results, which are all used in this method, are the same as those described above.

On the basis of the above described measurement results of autophagic activity, the action of a test substance to control skin or hair color can be evaluated. A test substance evaluated to have an influence on autophagic activity may be determined to be a substance having an action to control skin or hair color, or the test substance may be selected as an agent for controlling skin or hair color which can be used to control skin or hair color. Accordingly, the method for evaluating or selecting an agent for controlling skin or hair color according to the present invention may further comprise selecting the test substance as an agent for controlling skin or hair color, based on the evaluation results of the test substance.

For example, a substance which suppresses autophagic activity is selected as an agent for browning or darkening skin or hair color, which increases the amount of melanin in keratinocytes so as to brown or darken skin or hair color (e.g. a skin tanning agent, an agent for darkening hair color, an agent for returning bleached hair to natural hair color, a hair dye, etc.). Examples of such a substance include: a substance which suppresses the expression or activity of a gene associated with activation of autophagy or a molecule encoded thereby; and a substance which enhances the expression or activity of a gene associated with suppression of autophagic activity or a molecule encoded thereby.

On the other hand, a substance which enhances autophagic activity is selected as an agent for lightening skin or hair color, which decreases the amount of melanin in keratinocytes so as to lighten skin or hair color (e.g. a skin lightening agent, an agent for lighting or bleaching hair color, etc.). Examples of such a substance include: a substance which enhances the expression or activity of a gene associated with activation of autophagy or a molecule encoded thereby; and a substance which suppresses the expression or activity of a gene associated with suppression of autophagic activity or a molecule encoded thereby.

As exemplary embodiments of the present invention, the present specification discloses the following compositions, methods or intended uses. However, these embodiments are not intended to limit the scope of the present invention.

<1> A method for evaluating or selecting an agent for regulating the amount of melanin in a keratinocyte, comprising:
administering a test substance to a cell;
measuring a change in autophagic activity in the cell; and
evaluating an action of the test substance to regulate the amount of melanin, based on a result of the measurement.

<2> A method for evaluating an action of a test substance to regulate the amount of melanin in a keratinocyte, comprising:
administering a test substance to a cell;
measuring a change in autophagic activity in the cell; and
evaluating an action of the test substance to regulate the amount of melanin in a keratinocyte, based on a result of the measurement.

<3> The method according to <1> or <2> above, further comprising selecting the test substance as an agent for regulating the amount of melanin in a keratinocyte based on the evaluation result.

<4> The method according to any one of <1> to <3> above, wherein the test substance is evaluated to have an action to increase the amount of melanin in a keratinocyte in the following cases:

(i) a case in which the expression or activity of a gene associated with activation of autophagy or a molecule encoded thereby has been suppressed; or (ii) a case in which the expression or activity of a gene associated with suppression of autophagic activity or a molecule encoded thereby has been enhanced.

<5> The method according to any one of <1> to <3> above, wherein the test substance is evaluated to have an action to decrease the amount of melanin in a keratinocyte in the following cases:

(i) a case in which the expression or activity of a gene associated with activation of autophagy or a molecule encoded thereby has been enhanced; or (ii) a case in which the expression or activity of a gene associated with suppression of autophagic activity or a molecule encoded thereby has been suppressed.

<6> A method for evaluating or selecting an agent for controlling skin or hair color, comprising:
administering a test substance to a cell;
measuring a change in autophagic activity in the cell; and
evaluating an action of the test substance to control skin or hair color, based on a result of the measurement.

<7> A method for evaluating an action of a test substance to control skin or hair color, comprising:
administering a test substance to a cell;
measuring a change in autophagic activity in the cells; and
evaluating an action of the test substance to control skin or hair color, based on a result of the measurement.

<8> The method according to <6> or <7> above, further comprising selecting the test substance as an agent for controlling skin or hair color based on the evaluation result.

<9> The method according to any one of <6> to <8> above, wherein the test substance is evaluated to have an action to darken skin or hair color in the following cases:

(i) a case in which the expression or activity of a gene associated with activation of autophagy or a molecule encoded thereby has been suppressed; or (ii) a case in which the expression or activity of a gene associated with suppression of autophagic activity or a molecule encoded thereby has been enhanced.

<10> The method according to any one of <6> to <8> above, wherein the test substance is evaluated to have an action to lighten skin or hair color in the following cases:

(i) a case in which the expression or activity of a gene associated with activation of autophagy or a molecule encoded thereby has been enhanced; or (ii) a case in which the expression or activity of a gene associated with suppression of autophagic activity or a molecule encoded thereby has been suppressed.

<11> A method for regulating the amount of melanin in a keratinocyte, comprising regulating autophagic activity in a keratinocyte, wherein regulation of the amount of melanin is desired in the keratinocyte.

<12> The method according to <11> above, wherein regulating autophagic activity is increasing the amount of melanin in the keratinocyte by:

(i) suppressing the expression or activity of a gene associated with activation of autophagy or a molecule encoded thereby; or (ii) enhancing the expression or activity of a gene associated with suppression of autophagic activity or a molecule encoded thereby.

<13> The method according to <11> above, wherein regulating autophagic activity is decreasing the amount of melanin in the keratinocyte by:

(i) enhancing the expression or activity of a gene associated with activation of autophagy or a molecule encoded thereby; or (ii) suppressing the expression or activity of a gene associated with suppression of autophagic activity or a molecule encoded thereby.

<14> A method for controlling the skin or hair color of a subject, comprising regulating autophagic activity in the keratinocyte of a subject, wherein the subject desires to control skin or hair color.

<15> The method according to <14> above, wherein regulating autophagic activity is darkening skin color by:

(i) suppressing the expression or activity of a gene associated with activation of autophagy or a molecule encoded thereby; or (ii) enhancing the expression or activity of a gene associated with suppression of autophagic activity or a molecule encoded thereby.

<16> The method according to <14> above, wherein regulating autophagic activity is lightening skin color by:

(i) enhancing the expression or activity of a gene associated with activation of autophagy or a molecule encoded thereby; or (ii) suppressing the expression or activity of a gene associated with suppression of autophagic activity or a molecule encoded thereby.

<17> The method according to <15> or <16> above, wherein the keratinocyte is skin keratinocyte.

<18> The method according to <14> above, wherein regulating autophagic activity is darkening hair color by:

(i) suppressing the expression or activity of a gene associated with activation of autophagy or a molecule encoded thereby; or (ii) enhancing the expression or activity of a gene associated with suppression of autophagic activity or a molecule encoded thereby.

<19> The method according to <14> above, wherein regulating autophagic activity is lightening hair color by:

(i) enhancing the expression or activity of a gene associated with activation of autophagy or a molecule encoded thereby; or (ii) suppressing the expression or activity of a gene associated with suppression of autophagic activity or a molecule encoded thereby.

<20> The method according to <18> or <19> above, wherein the keratinocyte is follicular keratinocyte.

<21> The method according to any one of <11> to <20> above, wherein the method is a non-therapeutic method.

<22> Use of an autophagy-related gene or a molecule encoded by the gene, for regulating the amount of melanin in a keratinocyte.

<23> The use according to <22> above, for increasing or decreasing the amount of melanin.

<24> Use of an autophagy-related gene or a molecule encoded by the gene, for controlling skin or hair color.

<25> The use according to <24> above, for darkening or lightening skin or hair color.

<26> The use according to any one of <22> to <25> above, wherein the method is non-therapeutic use.

<27> An autophagy-related gene or a molecule encoded by the gene, for being used in regulating the amount of melanin in a keratinocyte.

<28> The gene or molecule according to <27> above, for being used in increasing or decreasing the amount of melanin.

<29> An autophagy-related gene or a molecule encoded by the gene, for being used in controlling skin or hair color.

<30> The gene or molecule according to <29> above, for being used in darkening or lightening skin or hair color.

<31> The method according to any one of <1> to <21> above, wherein the autophagic activity is selected from the group consisting of generation of a phagophore, the growth of a phagophore, formation of an autophagosome, the fusion of an autophagosome with a lysosome, formation of an autophagosome, and degradation of a substance in the inside of an autolysosome.

<32> The use according to any one of <22> to <26> above, wherein the autophagic activity is selected from the group consisting of generation of a phagophore, the growth of a phagophore, formation of an autophagosome, the fusion of an autophagosome with a lysosome, formation of an autolysosome, and degradation of a substance in the inside of an autolysosome.

<33> The gene or molecule according to any one of <27> to <30> above, wherein the autophagy-related gene is a gene associated with a step selected from the group consisting of generation of a phagophore, growth of a phagophore, formation of an autophagosome, fusion of an autophagosome with lysosomes, formation of an autolysosome, and degradation of a substance in the inside of an autolysosome in autophagy.

EXAMPLES

Hereinafter, the present invention will be more specifically described in the following examples.
Samples
(Neonatal Foreskin-Derived Normal Human Epidermal Keratinocytes; NHEKs)

Neonatal foreskin-derived normal human epidermal keratinocytes (NHEKs) were purchased from KURABO. The cells were placed on a 6-well plate at a density of $1 \times 10^5$ cells/well, and they were then cultured at 37° C. in 5% (v/v) $CO_2$ for 24 hours. The EpiLife medium (KURABO) [containing 10 μg/ml insulin, 0.1 μg/ml hEGF, 0.5 μg/ml hydrocortisone, 50 μg/ml gentamicin, 50 μg/ml amphotericin B, and 0.4% (v/v) bovine pituitary extract (BPE)] was used in the culture. After completion of the culture, the resulting cells were further cultured in a medium, from which BPE and hEGF had been removed, for 24 hours. Thereafter, the cultured cells were used in the subsequent experiment.
(Melanosomes)

Melanoma MNT-1 cells were provided from Dr. PiedGiorgio Natali (Regina Elena Institute, Rome, Italy) by the favor of him. The MNT-1 cells were cultured in an RPMI-1640 medium [containing 10% (v/v) FBS and 10% (v/v) AIM-V medium], and thereafter, melanosomes were isolated from the cultured cells.
(Neonatal Foreskin-Derived Keratinocytes; NHEKs)

The neonatal foreskins of Caucasian American and African American donors were obtained from National Disease Research Interchange (Philadelphia), and NHEKs were then prepared therefrom in accordance with the method described in Yoshida et al. (FASEB J 21: 2829-2839, 2007). Specifically, the foreskin was treated with Dispase to separate the epidermis from the corium, and the epidermal sheet was then treated at 37° C. for 10 minutes in 0.25% trypsin/EDTA solution to isolate cells. Thereafter, NHEKs were subjected to a primary culture using a special medium.
(Three-Dimensional Culture Human Skin Models)

Three-dimensional culture human skin models (3D-human skin substitutes; 3D-HSSs) were purchased from MatTek Co. (MEL-300A or B), and they were then maintained at 37° C. in 5% $CO_2$ in EPI-100NMM-113 medium (MatTek Co.) according to a production manual included therewith.

Reference Example 1

Association of Lysosome Mechanism in Melanin Degradation

The cultured NHEKs were cultured together with the MNT-1 cell-derived isolated melanosomes, in the presence or absence of lysosome inhibitors E-64-D and pepstatin A (20 μg/ml each). Twenty-four hours later, the cells were washed with PBS, and were further cultured in the presence or absence of E-64-D and pepstatin A (20 μg/ml each) for 24 hours. Thereafter, the cells were washed with PBS, and were then dissolved in RIPA buffer (Sigma-Aldrich) containing Protease Inhibitor Cocktail (Roche), followed by ultrasonic homogenization. Thereafter, a supernatant was recovered and was then separated by SDS-polyacrylamide electrophoresis. The separated sample was transcribed on Sequi-Blot (registered trademark) PVDF membrane (Bio-Rad), and Western blotting analysis was then carried out on the sample, using an antibody (clone HMB-45, DAKO Inc.) specific to a melanosomal protein Pmel-17.

In the Western blotting, the above described PVDF membrane was incubated with the Pmel-17-specific antibody (2000-fold diluted), was then washed, and was then incubated with a secondary antibody. As such a secondary antibody, peroxidase-bound anti-mouse IgG or peroxidase-bound anti-rabbit IgG (5000-fold diluted, GE Healthcare UK Ltd.) was used. The band was visualized using ECL Western blotting detection reagents (GE Healthcare UK Ltd.). Subsequently, the membrane was re-blotted with an antibody (Sigma-Aldrich) specific to β-actin loaded as an internal standard, and the amount of the loaded protein was then standardized.

Regarding some data, the relative intensity of the band of Pmel-17 obtained by the Western blotting analysis to the band of β-actin was obtained, and the amount of melanin accumulated was then quantified.

The results are shown in FIG. 1. By addition of the lysosome inhibitor, melanosomes were accumulated in NHEKs. These results suggested that the activity of lysosomes is associated with degradation of melanosomes in NHEKs.

Example 1

Difference in Expression of Autophagy-Related Factors Between Races Having Different Skin Colors The expression level of an autophagy-related factor ATG7 or ATG13 in the neonatal foreskin-derived keratinocytes (NHEKs) of Caucasian American and African American donors was examined.

NHEKs were cultured for 2 days. Then, Western blotting analysis was carried out on the cultured cells, using an ATG7-specific antibody (Epitomics Inc.) or an ATG13-specific antibody (MBL International) by the same procedures as those applied in Reference Example 1.

The results are shown in FIG. 2. The expression level of the autophagy-related factor was higher in NHEKs derived from a Caucasian American donor having light skin color than in NHEKs derived from an African American donor having dark skin color.

Example 2

Difference in Autophagic Activity Between Races Having Different Skin Colors Autophagic activity in the neonatal foreskin-derived keratinocytes (NHEKs) of Caucasian American and African American donors was examined.

NHEKs were cultured for 48 hours in the presence or absence of an autophagy inhibitor hydroxychloroquine (HCQ, 10 μM). Then, Western blotting analysis was carried out on the cultured cells, using a p62-specific antibody (2000-fold diluted, MBL International) or an LC3-specific antibody (2000-fold diluted, MBL International or Cosmo Bio Co., Ltd.), which served as a substrate of autophagy, by the same procedures as those applied in Reference Example 1. It is to be noted that, as LC3 proteins, LC3-I, and LC3-II formed by addition of phosphatidyl ethanolamine to the LC3-I, which was localized in autophagosomes, were detected. The relative intensity of each band obtained by Western blotting to the band of β-actin was obtained, and autophagic activity was then quantified.

The results are shown in FIG. 3. The results demonstrated that the amounts of p62 and LC3-II accumulated were higher in Caucasian American donor-derived NHEKs than in African American donor-derived NHEKs, in the presence of hydroxychloroquine serving as an autophagy inhibitor, and thus that the Caucasian American donor-derived NHEKs had high autophagic activity.

Example 3

Difference in Autophagic Activity after Uptake of Melanosomes Between Races Having Different Skin Colors The neonatal foreskin-derived keratinocytes (NHEKs) of Caucasian American and African American donors were cultured together with MNT-1 cell-derived isolated melanosomes for 0, 4, 8, 24 or 48 hours. Thereafter, the cultured cells were washed with PBS, and Western blotting analysis was then carried out on the resulting cells, using an LC3-specific antibody or a COX-IV-specific antibody (Abcam Inc.) by the same procedures as those applied in Reference Example 1. Each band in Western blotting was standardized to the band of β-actin, so as to obtain relative intensity.

The results are shown in FIG. 4. With addition of melanosomes, the amount of LC3-II was increased and the amount of COX-IV, which is known as a marker degraded by autophagic activity, was decreased in the Caucasian American donor-derived NHEKs. These results suggest that the Caucasian American donor-derived NHEKs had high autophagic activity and thus actively degraded melanin. On the other hand, in the African American donor-derived NHEKs, the amount of LC3-II was decreased due to melanosomes and autophagic activity was suppressed. Thus, these results suggest that melanin was actively accumulated in the cells. From the aforementioned results, it is considered that autophagic activity in keratinocytes will be associated with the amount of melanin on the skin, and skin color.

Example 4

Increase in Accumulation of Melanosomes in Keratinocytes by Suppression of Expression of Autophagy-Related Factors 10 nM ATG7-specific siRNA, ATG13-specific siRNA, UVRAG-specific siRNA, or non-specific siRNA (control) was transfected into NHEKs, using HiPerfect Transfection Reagent (QUIAGEN) in accordance with a production manual included therewith. Forty-eight hours later, MNT-1 cell-derived isolated melanosomes were added to the resulting cells, and the mixture was then cultured for 24 hours. Thereafter, the culture was washed with PBS so as to remove melanosomes which had not been taken up into the cells. The residue was further cultured for 24 hours. Thereafter, Western blotting analysis was carried out on the cultured cells, using an ATG7-specific antibody (Epitomics Inc.), an LC3-specific antibody (Cosmo Bio Co. Ltd. or MBL International), a p62-specific antibody (MBL international), or an antibody (clone HMB-45, DAKO Inc.) specific to Pmel17 as a melanosomal protein, by the same procedures as those applied in Reference Example 1. The results are shown in FIGS. 5A and B. By specific inhibition of the expression of ATG7, ATG13 and UVRAG, p62 serving as a substrate of autophagy was accumulated in keratinocytes, and the amount of Pmel17 was significantly increased.

10 nM ATG7-specific siRNA or non-specific siRNA (control) was transfected into NHEKs, and they were then cultured with the NHEMs for 7 days. Thereafter, the cells were washed with PBS and were then dried. The resultant was dissolved in Solvable™ (PerkinElmer), and the amount of melanin was then measured using an absorption spectrometer (Microplate Reader Model 550; Bio-Rad Laboratories). The results are shown in FIG. 5C. By inhibition of the ATG7 expression, the amount of melanin was increased in the co-culture of keratinocytes and melanocytes.

These results suggest that autophagy contribute to degradation of melanosomes in keratinocytes.

Example 5

Increase in Accumulation of Melanosomes in Keratinocytes by Suppression of Expression of Autophagy-Related Factors 100 pM, 1 nM, or 10 nM RAB11A-specific siRNA or ATG7-specific siRNA, or 10 nM non-specific siRNA (control) was transfected into NHEKs, using HiPerfect Transfection Reagent (QUIAGEN) in accordance with a production manual included therewith. Forty-eight hours later, MNT-1 cell-derived isolated melanosomes were added to the resulting cells, and the mixture was then cultured for 24 hours. Thereafter, the culture was washed with PBS so as to remove melanosomes which had not been taken up into the cells. The residue was further cultured for 24 hours. Thereafter, Western blotting analysis was carried out on the cultured cells, using an RAB11A-specific antibody (Life Technologies, Corp.), an ATG7-specific antibody (Epitomics Inc.), or an antibody (clone HMB-45, DAKO Inc.) specific to Pmel17, by the same procedures as those applied in Reference Example 1.

Figure 6:
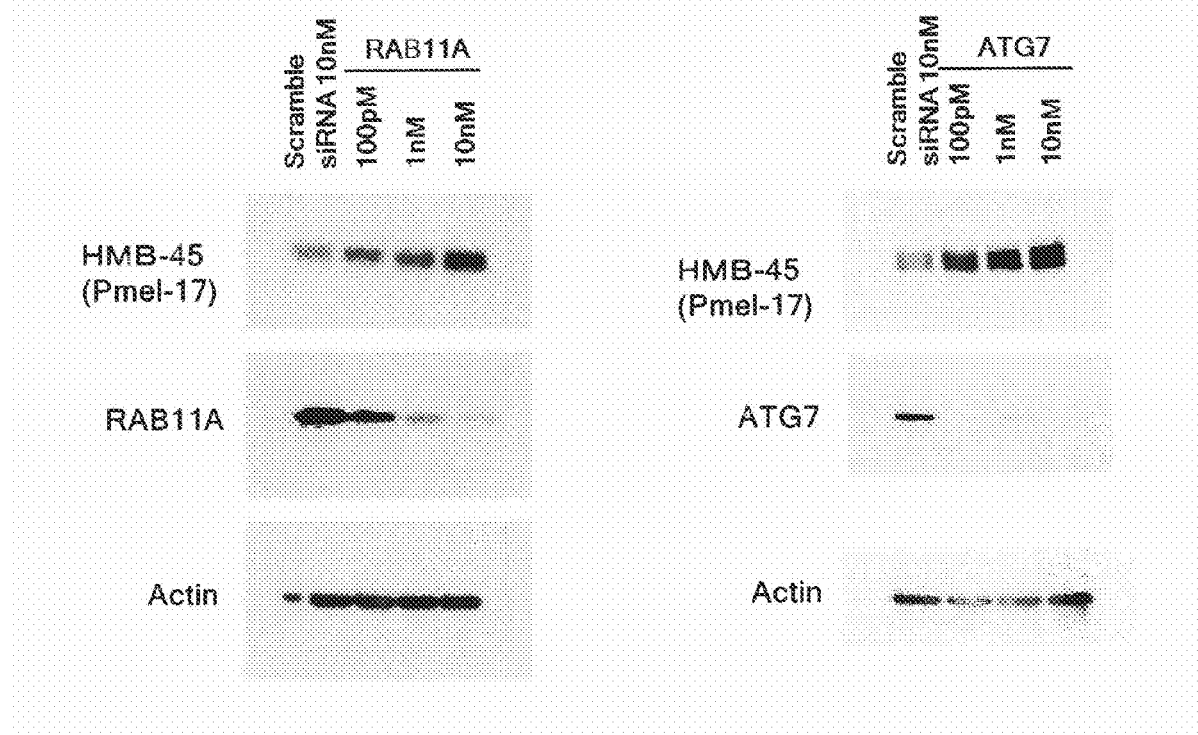
FIG. 6 shows an increase in accumulation of melanosomes due to suppression of the expression of autophagy-related factors.

The results are shown in FIG. 6. The amount of Pmel17 was increased depending on the siRNA concentrations of RAB11A and ATG7. These results suggest that there be a negative correlation between the autophagic activity level in keratinocytes and melanin accumulation.

Example 6

Increase in Accumulation of Melanosomes in Keratinocytes by Suppression of Expression of Autophagy-Related Factors 10 nM ATG5-specific siRNA, UVRAG-specific siRNA, or non-specific siRNA (control) was transfected into the cultured NHEKs, using HiPerfect Transfection Reagent (QUI-AGEN) in accordance with a production manual included therewith. Forty-eight hours later, MNT-1 cell-derived isolated melanosomes were added to the resulting cells, and the mixture was then cultured for 24 hours. Thereafter, the culture was washed with PBS so as to remove melanosomes which had not been taken up into the cells. The residue was further cultured for 24 hours. Thereafter, Western blotting analysis was carried out on the cultured cells, using Pmel17-specific antibody (clone HMB-45, DAKO Inc.) by the same procedures as those applied in Reference Example 1.

Figure 7:
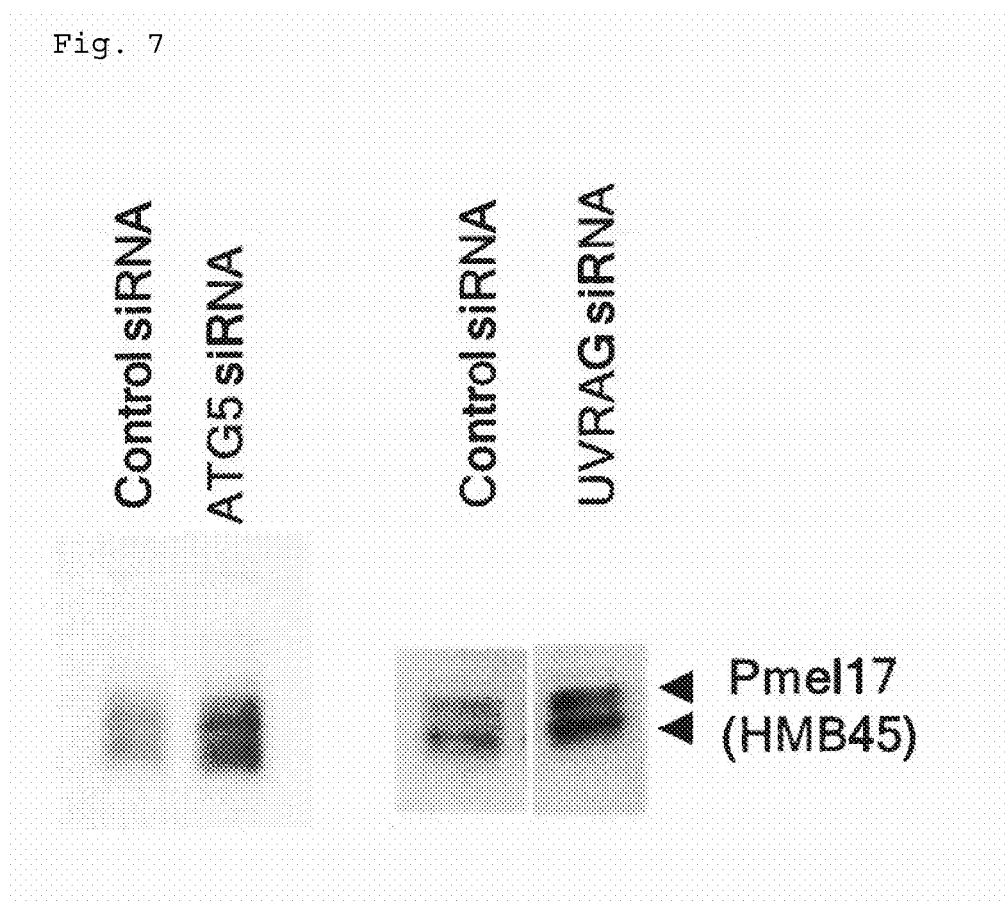
FIG. 7 shows an increase in accumulation of melanosomes due to suppression of the expression of autophagy-related factors.

The results are shown in FIG. 7. By specific inhibition of ATG5 or UVRAG, the amount of Pmel17 (clone; HMB45) was significantly increased. These results suggest that autophagy-related factors contribute to degradation of melanosomes in NHEKs.

Example 7

Increase in Accumulation of Melanosomes in Keratinocytes by Activation of Autophagy The influence of suppression of mTOR as an autophagy-suppressing factor on melanin accumulation was examined. 10 nM mTOR-specific siRNA or non-specific siRNA (control) was transfected into the cultured NHEKs, using HiPerfect Transfection Reagent (QUIAGEN) in accordance with a production manual included therewith. Twenty-four hours later, MNT-1 cell-derived isolated melanosomes were added to the resulting cells, and the mixture was then cultured for 24 hours. Thereafter, the culture was washed with PBS so as to remove melanosomes which had not been taken up into the cells. The residue was further cultured for 24 hours. Thereafter, Western blotting analysis was carried out on the cultured cells, using an LC3-specific antibody (Cosmo Bio Co. Ltd. or MBL International) and an antibody (clone HMB-45, DAKO Inc.) specific to Pmel17 by the same procedures as those applied in Reference Example 1. Each band obtained by Western blotting was standardized to the band of β-actin, so as to obtain relative intensity.

The results are shown in FIG. 8. Autophagic activity was promoted by specific inhibition of mTOR serving as an autophagy-suppressing factor. As a result, the amount of LC3-II was increased, and the amount of Pmel17 was significantly decreased. These results suggested that mTOR have influence on the amount of melanin accumulated, via an autophagic mechanism.

Example 8

Influence of Autophagy Regulation on Amount of Melanin in Three-Dimensional Culture Human Skin Models (3D-HSSs)

3D-HSSs (three-dimensional human skin substitutes, reconstituted epidermal models containing NHEK and NHEM) were cultured together with an autophagy inducer verapamil (10 μM) or rapamycin (1 μM) for 14 days. The medium was exchanged with a fresh one every other day. After completion of the culture, Western blotting analysis was carried out on the culture, using a p62-specific antibody (MBL International) and an LC3-specific antibody (Cosmo Bio Co. Ltd. or MBL International) by the same procedures as those applied in Reference Example 1.

On the other hand, 3D-HSSs were cultured together with an autophagy inhibitor hydroxychloroquine (HCQ, 10 μM) in the presence of endothelin-1 and SCF for 14 days, and Western blotting analysis was then carried out on the culture.

The results are shown in FIG. 9. With the presence of the autophagy inducer, the darkening of 3D-HSSs was suppressed (FIG. 9A, 14 days after completion of the culture). In addition, the amount of LC3-II which was an indicator of autophagic activity was increased, and the amount of a substrate protein p62 which was degraded by autophagy was decreased (FIG. 9B, 6 days after completion of the culture). On the other hand, with the presence of the autophagy inhibitor HCQ, 3D-HSSs became darkened, and the amount of p62 was increased (FIGS. 9C and D).

Example 9

Influence of Autophagy Regulation on Human Skin Color

Skin tissues were collected from an African American donor, and were then cultured in the presence or absence of an autophagy inducer verapamil (10 μM) or rapamycin (1 μM), or an autophagy inhibitor hydroxychloroquine (HCQ, 10 μM). After completion of the culture for 8 days, the lightness ($L^*$ value) of the cultured skin was measured with a colorimeter (Colorimeter; cyberDERM). The results are shown in FIG. 10. The $L^*$ value of the skin cultured together with the autophagy inducer was increased (namely, the skin color became lightened). On the other hand, the $L^*$ value of the skin cultured together with the autophagy inhibitor was decreased (namely, the skin color became darkened).

Example 10

Evaluation or Selection of Agent for Regulating the Amount of Melanin

A test substance was added to the cultured NHEKs, and the obtained mixture was then cultured for 72 hours. After completion of the culture, the cells were washed with PBS, and were then dissolved in RIPA buffer (Sigma-Aldrich) containing Protease Inhibitor Cocktail (Roche), followed by ultrasonic homogenization so as to recover a supernatant. Thereafter, with regard to the amount of RAB11A or ATG7 in the recovered supernatant, Western blotting analysis was carried out. With regard to cells which had been cultured without addition of such a test substance (control), the amount of RAB11A or ATG7 was measured by the same procedures as described above. A test substance, which suppressed the amount of RAB11A or ATG7 30% or more stronger than in the case of the control, was selected as a candidate substance for an agent for increasing the amount of melanin. As a result, 15 types of test substances were selected as candidate substances.

Figure 11:
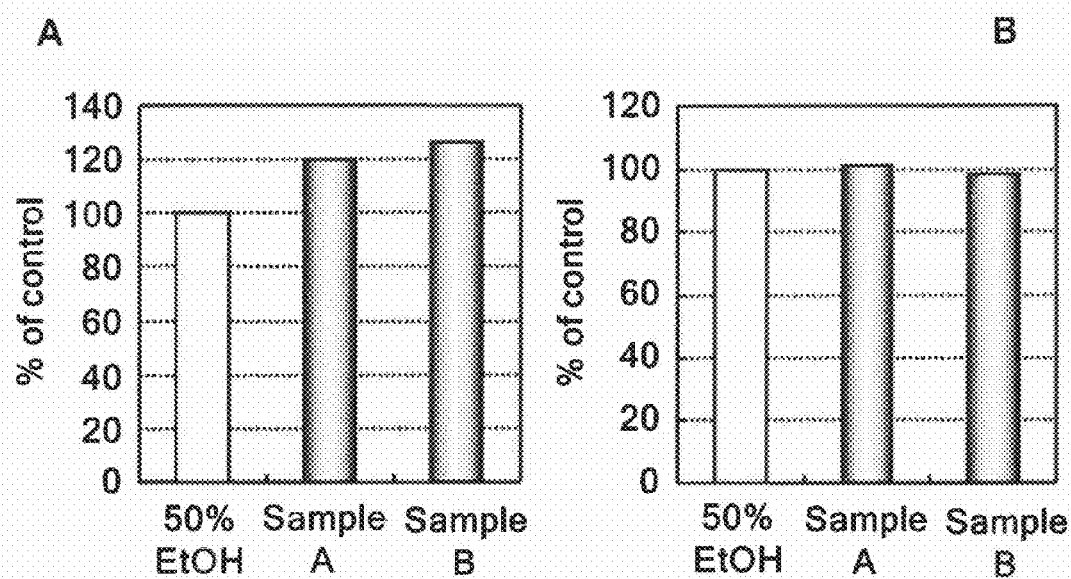
FIG. 11 shows the control of skin color by an agent for regulating the amount of melanin selected by the selection method of the present invention. A: the amount of melanin; B: cellular respiratory activity.

The activity of each selected candidate substance to regulate the amount of melanin was examined. Specifically, the selected candidate substance was added only to the upper portion (horny cell layer side) of 3D-HSSs containing NHEK and NHEM, and it was then cultured for 14 days. After completion of the culture, the tissues were solubilized in a sodium hydroxide (2 N) aqueous solution, so as to measure the amount of melanin in the tissues. Also, the cellular respiratory activity of 3D-HSSs which had been cultured with the addition of a candidate substance was measured according to an Alamar Blue method, so as to examine the cytotoxicity of the candidate substance. The results of two types of candidate substance samples A and B are shown in FIG. 11. It was confirmed that the candidate substances have an activity of increasing the amount of melanin. Moreover, as a result of the measurement of the cellular respiratory activity, it was confirmed that these candidate substances have no cytotoxicity.

The embodiments of the present invention are described above. However, it should be understood that these embodiments are not intended to limit the scope of the present invention to the above described specific embodiments. It is obvious to a person skilled in the art that various other alternations and modifications are included in the scope of the present invention.

All publications and patent applications cited in the present specification are incorporated herein by reference in their entirety.

What is claimed is:

1. A method for evaluating or selecting an agent that regulates the amount of melanin in a keratinocyte, comprising:
   (a) administering a test substance to a keratinocyte;
   (b) measuring a change in autophagic activity in the keratinocyte; and
   (c) evaluating or selecting the test substance as an agent that regulates the amount of melanin by increasing the amount of melanin in a keratinocyte when the test substance decreases expression or activity of a gene associated with activation of autophagy in the keratinocyte, or when the test substance increases expression of a gene associated with suppression of autophagy in the keratinocyte, or
   evaluating or selecting the test substance as an agent that regulates the amount of melanin by decreasing the amount of melanin in a keratinocyte when the test substance increases expression or activity of a gene associated with activation of autophagy in the keratinocyte, or when the test substance decreases expression of a gene associated with suppression of autophagy in the keratinocyte.

2. The method according to claim 1, wherein the test substance is evaluated or selected as an agent that increases the amount of melanin in a keratinocyte.

3. The method according to claim 1, wherein the test substance is evaluated or selected as an agent that decreases the amount of melanin in a keratinocyte.

4. A method for evaluating or selecting an agent that controls skin or hair color, comprising:
   (a) administering a test substance to a keratinocyte;
   (b) measuring autophagic activity in the keratinocyte; and
   (c) evaluating or selecting the test substance as an agent that controls skin or hair color by darkening skin or hair color when the test substance decreases expression or activity of a gene associated with activation of autophagy in the keratinocyte, or when the test substance increases expression of a gene associated with suppression of autophagy in the keratinocyte, or
   evaluating or selecting the test substance as an agent that controls skin or hair color by lightening skin or hair color when the test substance increases expression or activity of a gene associated with activation of autophagy in the keratinocyte, or when the test substance decreases expression of a gene associated with suppression of autophagy in the keratinocyte.

5. The method according to claim 4, wherein the test substance is evaluated or selected as an agent that darkens skin or hair color.

6. The method according to claim 4, wherein the test substance is evaluated or selected as an agent that lightens skin or hair color.

7. The method of claim 4, wherein the test substance is evaluated or selected as an agent that darkens hair color.

8. The method of claim 4, wherein the test substance is evaluated or selected as an agent that lightens hair color.

9. The method of claim 4, wherein the test substance is evaluated or selected as an agent that darkens skin color.

10. The method of claim 4, wherein the test substance is evaluated or selected as an agent that lightens skin color.

* * * * *